US008460270B2

(12) United States Patent
Müller et al.

(10) Patent No.: US 8,460,270 B2
(45) **Date of Patent: *Jun. 11, 2013**

(54) SYSTEM, APPARATUS, AND METHOD FOR FACILITATING INTERFACE WITH LARYNGEAL STRUCTURES

(75) Inventors: Andreas Müller, Jena (DE); Gerhard Förster, Jena (DE)

(73) Assignee: MED-EL Elektromedizinische Gerete GmbH, Innsbruck (AT)

( * ) Notice: Subject to any disclaimer, the term of this patent is extended or adjusted under 35 U.S.C. 154(b) by 1154 days.

This patent is subject to a terminal disclaimer.

(21) Appl. No.: 11/848,116

(22) Filed: Aug. 30, 2007

(65) Prior Publication Data

US 2008/0071245 A1 Mar. 20, 2008

Related U.S. Application Data

(60) Provisional application No. 60/824,064, filed on Aug. 30, 2006, provisional application No. 60/824,065, filed on Aug. 30, 2006, provisional application No. 60/824,066, filed on Aug. 30, 2006, provisional application No. 60/824,067, filed on Aug. 30, 2006, provisional application No. 60/824,072, filed on Aug. 31, 2006.

(51) Int. Cl.
*A61M 31/00* (2006.01)

(52) U.S. Cl.
USPC ................ 604/506; 604/500; 128/898; 623/9

(58) Field of Classification Search
USPC ................ 604/500, 506; 128/898, 902; 623/9
See application file for complete search history.

(56) References Cited

U.S. PATENT DOCUMENTS

| | | | | |
|---|---|---|---|---|
| 4,280,503 | A | 7/1981 | Ackerman | |
| 4,488,561 | A | 12/1984 | Doring | |
| 5,111,814 | A * | 5/1992 | Goldfarb | 607/48 |
| 5,443,493 | A | 8/1995 | Byers et al. | |
| 5,897,579 | A | 4/1999 | Sanders | |
| 6,078,841 | A | 6/2000 | Kuzma | |
| 6,973,346 | B2 * | 12/2005 | Hafer et al. | 604/21 |
| 6,978,787 | B1 | 12/2005 | Broniatowski | |
| 2003/0045892 | A1 | 3/2003 | Kaladelfos | |
| 2003/0120195 | A1 | 6/2003 | Milo et al. | |
| 2006/0254595 | A1 | 11/2006 | Rea | |

(Continued)

FOREIGN PATENT DOCUMENTS

| | | | |
|---|---|---|---|
| CA | 2414898 | A1 | 9/2002 |
| WO | 9635469 | A1 | 11/1996 |
| WO | 9728746 | A1 | 8/1997 |
| WO | 00/71063 | A1 | 11/2000 |

(Continued)

OTHER PUBLICATIONS

International Search Report dated Feb. 26, 2008.

*Primary Examiner* — Bhisma Mehta
*Assistant Examiner* — Larry R Wilson
(74) *Attorney, Agent, or Firm* — Sunstein Kann Murphy & Timbers LLP

(57) ABSTRACT

A system and method of introducing interface elements for interfacing with laryngeal structures of a subject is presented. Illustratively, a tunnel is generated in geographical relation to the lateral wing of the thyroid cartilage of the subject and at least one interface element is introduced via the tunnel for interfacing with at least one laryngeal structure of the subject.

9 Claims, 27 Drawing Sheets

U.S. PATENT DOCUMENTS

| | | | | |
|---|---|---|---|---|
| 2006/0282127 | A1 * | 12/2006 | Zealear | 607/42 |
| 2007/0078503 | A1 | 4/2007 | Kuzma et al. | |
| 2007/0123950 | A1 | 5/2007 | Ludlow et al. | |
| 2007/0156041 | A1 | 7/2007 | Rea | |

FOREIGN PATENT DOCUMENTS

| | | | |
|---|---|---|---|
| WO | 0158516 | A1 | 8/2001 |
| WO | 03/070133 | A1 | 8/2003 |

* cited by examiner

SYSTEM, APPARATUS, AND METHOD FOR FACILITATING INTERFACE WITH LARYNGEAL STRUCTURES

CROSS-REFERENCE TO RELATED APPLICATIONS

This application claims priority from the following United States Provisional Patent Applications, all of which are hereby incorporated herein by reference in their entireties:

U.S. Provisional Patent Application No. 60/824,064 entitled Electrode Insertion System and Method for Vocal Chord Stimulation filed Aug. 30, 2006 in the names of Müller and Förster;

U.S. Provisional Patent Application No. 60/824,065 entitled Electrode Insertion System and Method for Vocal Chord Stimulation filed Aug. 30, 2006 in the names of Müller and Lindenthaler;

U.S. Provisional Patent Application No. 60/824,066 entitled Electrode Insertion System and Method for Vocal Chord Stimulation filed Aug. 30, 2006 in the name of Müller and Förster;

U.S. Provisional Patent Application No. 60/824,072 entitled Electrode Insertion System and Method for Vocal Chord Stimulation filed Aug. 31, 2006 in the name of Lindenthaler; and U.S. Provisional Patent Application No. 60/824,067 entitled Electrode Insertion System and Method for Vocal Chord Stimulation filed Aug. 30, 2006 in the name of Hagen.

This application is also related to the following U.S. patent applications, all of which are being filed on even date herewith and are hereby incorporated herein by reference in their entireties:

U.S. patent application Ser. No. 11/848,116 entitled System, Apparatus, and Method for Facilitating Interface with Laryngeal Structures filed in the names of Lindenthaler and Förster;

U.S. patent application Ser. No. 11/848,108 entitled System, Apparatus, and Method for Facilitating Interface with Laryngeal Structures filed in the names of Lindenthaler and Müller;

U.S. patent application Ser. No. 11/848,126 entitled System, Apparatus, and Method for Facilitating Interface with Laryngeal Structures filed in the name of Lindenthaler; and U.S. patent application Ser. No. 11/848,065 entitled System, Apparatus, and Method for Facilitating Interface with Laryngeal Structures filed in the names of Müller, Förster, and Hagen.

FIELD OF THE INVENTION

The invention generally relates to an insertion system for laryngeal structures and, more particularly, the invention relates to an interface element (such as an electrode) insertion system and method for facilitating an interface with laryngeal structures (such as vocal cord stimulation).

BACKGROUND OF THE INVENTION

Functional electrical stimulation ("FES") is the application of stimulation devices to nerves and muscles to treat medical disorders. The most successful FES system to date is the cardiac pacer which has become a routine part of cardiac disease therapy: Lynch, *Cardiovascular Implants*, in *Implants*, Lynch ed., Van Nostrand Rheinhold, New York 1982, incorporated herein by reference. However, there are a variety of other FES systems. The most heavily researched are FES systems to restore locomotion to paraplegics and arm motion to quadriplegics: Peckham, IEEE Trans. Biomed. Eng. 1991, 28: 530, incorporated herein by reference. Other motor control devices restore bladder control to paraplegics and diaphragm function to high quadriplegics: Erlandson, Scand. J. Urol. Nephrol. 44 Suppl: 31, 1978; Glenn, Ann. Surg. 183: 566, 1976, incorporated herein by reference. There are also FES devices designed to rehabilitate the sensory deficits, such as the cochlear implant: Hambrecht, Ann. Otol. Rhinol. Laryngol. 88: 729, 1979, incorporated herein by reference.

The recurrent laryngeal nerve, which innervates the larynx, contains motor fibers that innervate both the abductor/opener and adductor/closer muscles of the vocal folds. Damage to this nerve compromises both of these functions and arrests the vocal fold just lateral to the midline. In unilateral paralysis, the voice is breathy and aspiration can occur because of compromised adduction, but airflow during inspiration is minimally impaired. Adequate ventilation of the lungs is assured because abduction of the opposite fold can still occur with each inspiration. In bilateral paralysis, there is a loss of abductory function in both folds, the voice may be minimally impaired because of fold symmetry and their paramedian position in most of the patients, but airway discomfiture is usually severe. Typically, the patient can tolerate restricted activity or may be relegated to a sedentary lifestyle until treatment is administered. In some situations, however, the condition may be life-threatening.

Clinical management of vocal fold paralysis focuses on the major laryngeal dysfunction associated with each of these two main types. Conventional treatments for unilateral paralysis aim at medializing the fold to improve voice production. Treatment for bilateral paralysis typically requires a tracheotomy to restore sufficient airflow to the lungs. The tracheotomy is left in place until nerve regeneration and muscle reinnervation has returned. However, in many cases, muscle reinnervation is either incomplete or inappropriate resulting in chronic paralysis. Under such conditions, surgical resection of the vocal fold (i.e., cordotomy) is employed to permanently increase the airway and relieve the patient of his tracheotomy. Although these conventional methods of treatment have been useful, they are less than ideal, since they tend to improve upon one laryngeal function at the expense of another. For example, cordotomy improves ventilation, but compromises voice production and airway protection.

Surgical techniques, such as laser arytenoidectomy and partial cordectomy, can be performed to widen the airway and relieve dyspnea in the case of chronic paralysis. However, these procedures compromise voice and airway protection to restore ventilation through the mouth. They also ignore the long-term effects of ensuing atrophy on vocal fold mass and position. In general, the greater the cartilaginous or membranous resection associated with either technique, the greater the morbidity. A number of modifications of these two strategies have been devised in an attempt to strike a more delicate balance between improved oral ventilation and impaired voice and swallowing. However, a more conservative stance toward resection increases the probability of failed intervention and the necessity for revision surgery. A new, more physiological approach termed laryngeal pacing has been studied in animal models as a means to restore oral ventilation.

Application of FES to paralyzed laryngeal muscles was introduced into human clinical otolaryngology in 1977 by Zealear D L, Dedo H H, *Control Of Paralyzed Axial Muscles By Electrical Stimulation*, Acta Otolaryngol (Stockholm) 1977, 83:514-27, incorporated herein by reference, which specifically addressed the case of unilateral vocal fold paralysis. Patients normally breathe well, but they cannot approximate both vocal folds. As a result, their voice is weak and breathy, and they tend to aspirate fluids. Zealear and Dedo proposed that a unilaterally paralyzed patient could be reanimated to close appropriately by electrical stimulation triggered by signals relayed from its contralateral partner. As simpler surgical methods were discovered to restore function in unilateral vocal fold paralysis, the development of an implantable neuroprostheses for this condition has not been vigorously pursued.

Mayr, Zrunek, et al., *A Laryngeal Pacemaker For Inspiration Controlled Direct Electrical Stimulation Of Denervated Posterior Cricoarytaenoid Muscle In Sheep*, Eur. Arch. Otorhinolaryngol, 248(8):445-448, 1991, incorporated herein by reference, described 8 sheep with denervated PCAs which received implants for from 5-18 months, and ruled out reinnervation by control.

Obert et al., *Use Of Direct Posterior Cricoarytenoid Stimulation In Laryngeal Paralysis*, Arch. Otolaryngol 1984, 110: 88-92, incorporated herein by reference, restored full abduction in bilaterally denervated dogs implanted with single-stranded teflon electrodes, using 20 ms stimulus pulses delivered at 20-40 Hz and 2-3 mA. Their study suggested that stimulus pulses should be synchronized with inspiratory signals in abductor pacing. Bergmann et al., *Respiratory Rhythmically Regulated Electrical Stimulation Of Paralyzed Muscles*, Laryngoscope, 1984, 94:1376-80, incorporated herein by reference, successfully implanted this idea of respiratory regulation of stimuli, using signals relayed from chest wall expansion. Canine PCA muscles were activated using parameters of 30 Hz, 1 ms, and large amplitudes of up to 50 mA.

Kano and Sasaki, *Pacing Parameters of the Canine Posterior Cricoarytenoid Muscle*, Ann. Otol. Rhinol. Laryngol., 100:584-588, 1991, incorporated herein by reference, used a pair of coiled electrodes, separated by 2 mm, to stimulate the PCA. They observed promising abductions at 60-90 Hz and 2 ms. Bergmann et al reported 2-3 mm of abduction with stimulation of the PCA using a stimulus delivery system that had been chronically implanted for 11 months.

Otto et al, *Coordinated Electrical Pacing Of Vocal Cord Abductors In Recurrent Laryngeal Nerve Paralysis*, Otolaryngol. Head Neck Surg., 1985, 93:634-8, incorporated herein by reference, used electromyographic (EMG) signals from the diaphragm to regulate stimuli to denervated canine PCA muscles, and reportedly restored full abduction of the glottis.

Zealear and Herzon, *Technical Approach For Reanimation Of The Chronically Denervated Larynx By Means Of Functional Electrical Stimulation*, Ann. Otol. Rhinol. Laryngol., 1994 September, 103(9):705-12, incorporated herein by reference, first introduced use of tiny coiled electrodes for abductor pacing in a study of inspiratory trigger sources including tracheal elongation, diaphragm EMG signals, phrenic nerve activity, and intrathoracic pressure changes.

Zealear et al, *Technical Approach For Reanimation Of The Chronically Denervated Larynx By Means Of Functional Electrical Stimulation*, Ann. Otol. Rhinol. Laryngol. 1994, 103:705-12, incorporated herein by reference, implanted an electrode array 3 months after RLN section, and the paralyzed stump was electro stimulated to rule out reinnervation. The hot spots were located in the middle of the PCA muscle, several millimeters from the median raphe, and covered 30-40% of the muscle surface area.

During chronic pacing, it would be desirable to stimulate above the fusion frequency for the PCA muscle so that a smooth abduction of the vocal cord would be achieved. In each animal, the chronically denervated muscle had a lower fusion frequency than its innervated partner. In a chronic implant, it would be desirable to lower the rate of stimulation under 30 Hz closer to that of the fusion frequency (mean: 21.77 Hz) to conserve charge. FIG. 3 shows views of a clinical patient with laryngeal hemiplegia both at rest and during stimulation with 4.5 mA at 24 Hz. As the pulse duration was increased, the efficiency in activating chronically denervated muscle increased and surpassed that of the innervated muscle at durations greater than 1-2 ms. However above 2 ms, stimulation became less efficient for both muscles because of charge loss through current shunts normally found in tissue. The amount of vocal cord excursion was only 40-70% of that produced with stimulation of the normally innervated muscle, indicative of denervation atrophy and loss of muscle contractility.

Sanders I et al., *Arytenoid Motion Evoked By Regional Electrical Stimulation Of The Canine Posterior Cricoarytenoid Muscle*, Laryngoscope. 1994 April; 104(4):456-62, incorporated herein by reference, systematically evaluated stimulation delivered to the denervated canine PCA muscles, using single-stranded, stainless steel electrodes 1 cm in length. Measures of abduction were obtained following an overdose of curare designed to mimic vocal fold paralysis via neuromuscular blockade. After RLN section and 2 weeks' time, measures of abduction were repeated in these animals. Results documented 3 mm of vocal cord excursion with 1 ms, 30 Hz, and 1-50 mA.

Sanders I., *Electrical Stimulation Of Laryngeal Muscle*, Otolaryngol Clin North Am. 1991 October; 24(5):1253-74, incorporated herein by reference, left 4 dogs undisturbed for 6 months to allow atrophy to occur. After 6 months of atrophy, the responses of the animals had decreased to roughly 60% of initial values. The two dogs that did not undergo stimulation continued to atrophy during the following 4 months to 40% of initial values. The two dogs that underwent electrically induced exercise, however, increased their responses dramatically. Not only had their responses returned to normal, but they were uniformly greater than normal, the average approximately 200% that of their initial denervated state. Gross examination of the excised larynges demonstrated that the stimulated group had maintained muscle bulk while the non-stimulated group was noticeably atrophic. Denervated dog PCA could be stimulated with pulses as short as 2 ms. Any lower, and the needed voltage jumped exponentially. Sanders used similar pulse widths to chronically stimulate denervated muscle for months. This is the minimum and presupposes that the electrode is placed directly adjacent to the muscle.

Zealear D L et al., *Reanimation Of The Paralyzed Human Larynx With An Implantable Electrical Stimulation Device*, Laryngoscope. 2003 July; 113(7):1149-56, incorporated herein by reference, reported on four human patients implanted with adapted pain pacemaker systems. In the four patients tested, electromyographic (EMG) motor unit activity was present in the PCA and thyroarytenoid (TA) muscles during voluntary effort. These recordings showed inappropriate firing patterns. For example, inspiratory motor unit activity was recorded from the TA muscle characteristic of a PCA motor unit. In particular, a deep inspiration or sniff increased the rate of firing of individual motor units and enhanced the overall interference response. This inappropriate activity was indicative of synkinetic reinnervation.

In follow-up sessions, the optimum stimulus parameters for vocal fold abduction were studied. A one- to two-second train of one-millisecond pulses delivered at a frequency of 30 to 40 pulses per second (pps) and amplitude of 2 to 7 V effectively produced a dynamic airway. One to two seconds of stimulated abduction allowed sufficient air exchange with each breath. Although a previous study in the canine found 2-millisecond duration as the optimum pulse width for recruiting both reinnervated and non-reinnervated muscle fibers, the maximum pulse width that the stimulator could deliver was 1 millisecond. A frequency of 30 to 40 pps generated a fused, tetanising muscle contraction and a smooth vocal fold abduction with maximum opening. The device was set to deliver an average of 10 stimulus sequences (bursts) every minute to match the patient's respiratory rate at a moderate level of activity. The ideal stimulus amplitude was one that evoked maximum vocal fold opening without inducing discomfort or nociception. At this amplitude, the patient could feel the stimulus, which helped entrain inspiration to the stimulus cycle. Stimulated abduction significantly increased the magnitude of glottal opening in patients 1 to 5 from preoperative levels ($P<0.0008$). Stimulated glottal opening was large in patients 1, 3, and 4 (3.5-7 mm) and moderate in patient 2 (3 mm). In patient 5, stimulation also produced a large abduction of 4 mm, but the response was delayed in time.

In order to decrease current spread and the high power requirements of FES devices, the placement of electrodes should localize current to the target muscle or nerve (if the muscle is innervated—even if it is synkinetically reinnervated) as much as possible. This may be accomplished by placing the electrodes inside the muscle, or on its surface, a procedure that produces two technical problems: (1) surgical exposure of the muscle causes scarring which eventually decreases muscle mobility; and (2) because electrodes must be close to their target to be efficient, they are exposed to muscle movement. The constant abrasion of the electrode against the muscle breaks the electrode or causes extensive fibrosis in the muscle. This difficulty plagued the early development of the cardiac pacer and persists today in many experiments involving chronic stimulation of denervated muscle, including the denervated PCA. As a result, there has not been a truly successful chronic device for stimulation of denervated muscle.

In 1992 for unilateral vocal cord paralysis, Goldfarb used the electric activity of the healthy side as a trigger for synchronization with breathing and vocalization. See, U.S. Pat. No. 5,111,814. This method is not applicable for the clinically more relevant bilateral paralysis. Lindenthaler described a pacemaker for bilateral vocal cord palsy due to autoparalysis (equivalent to synkinetic Recurrent Laryngeal Nerve (RLN) reinnervation), which is triggered by another muscle or nerve signal that is activated synchronic to breathing, e.g., diaphragm breathing muscles, infrahyoidal muscles of the neck. The pacemaker then stimulates structurally intact but autoparalytic nerve. See, U.S. Pat. No. 7,069,082.

For a real and complete rehabilitation of some patients with uni- or bilateral vocal cord paralysis or even in patients with a larynx transplantation a mere restoration of a single movement function of vocal cords by a pacemaker is not sufficient. In some cases even essential, is a pacemaker that can stimulate opening of vocal cords (e.g., to achieve sufficient breath for physical activities) as well as complete closure and tension of vocal cords (e.g., for vocalization and in combination with larynx elevation during swallowing for protection against aspiration). An optimal coordination of stimulated larynx movements with breathing cycle, intentional vocalization and swallowing reflex is necessary for that.

A stimulation of opening and closing of vocal cords might be helpful to preserve the full dynamic range of vocal cord movability by preventing a fixation of the cricoarytenoid joint. The necessary electrodes or sensing devices for detecting triggers and for stimulation of autoparalytic nerves or direct stimulation of paralyzed muscles of the larynx itself must not damage healthy tissue. In addition, the implantation procedure should also not cause harm.

Current surgical techniques all involve the exposure of the endings of the RLN or the exposure of the opening muscle (i.e., Posterior Cricoarytenoid Muscle, (PCA)) of the larynx. To achieve this, other muscles have to be cut (e.g., infrahyoidal muscles or pharyngeal constrictor muscle) and vessels and nerves in the vicinity may be damaged causing an impaired mobility of the larynx during swallowing and impaired sensitivity of mucus membranes with an increased risk of foreign body aspiration. Furthermore, scarring of all those tissues may diminish stimulated movements in the long run.

In addition, free placement of electrodes through the tissue to the target muscle (or nerve) may cause a high mechanical stress in the electrode leads which may cause lead wire breakage in delicate electrodes. Thus, placing or laying of the electrode in such a way that protects the electrode more may be helpful.

In order to decrease current spread and the high power requirements of FES devices, the placement of electrodes should localize current to the target muscle or nerve (if the muscle is innervated—even if it is synkinetically reinnervated) as much as possible. This may be accomplished by placing the electrodes inside the muscle or at its surface, a procedure that produces two technical problems: (1) surgical exposure of the muscle causes scarring which eventually decreases the muscle's mobility; and (2) because electrodes must be close to their target to be efficient, they are exposed to muscle movement. The constant abrasion of the electrode against muscle breaks the electrode or causes extensive fibrosis in the muscle. This difficulty plagued the early development of the cardiac pacer and persists today in many experiments involving chronic stimulation of denervated muscle, including the denervated PCA. As a result, there is not currently a truly successful chronic device for stimulation of denervated muscle.

An open surgery is much more invasive than a needle insertion. Insertion needles or puncture needles are typically straight and not curved, consisting of one part. For some situations, however, it is not possible to reach the target point (e.g., inside the subject's body or a different position outside the body then where the insertion started) in a straight line from the outside of the body or starting from cavities inside the body.

SUMMARY OF THE INVENTION

In accordance with one aspect of the invention there is provided a method of introducing interface elements for interfacing with laryngeal structures of a subject such as for diagnosis or treatment of a laryngeal impairment. The method involves generating a tunnel in geographical relation to the lateral wing of the thyroid cartilage of the subject and introducing at least one interface element via the tunnel for interfacing with at least one laryngeal structure of the subject.

The tunnel may be generated at least in part by introduction of an interface element. In various alternative embodiments, a portion of the tunnel may be medial of the thyroid cartilage. The tunnel may include a part of a subperichondral tunnel on an inside of thyroid cartilage lamina. The tunnel may include a part of a subperichondral tunnel on an outside of thyroid cartilage lamina. The tunnel may include a part of a tunnel drilled inside of a thyroid cartilage wall, for example, formed in a curve in the inside of the thyroid cartilage wall. The tunnel may be drilled partly inside of a cricoid cartilage wall and may include a subperichondral tunnel on an inside of cricoid cartilage lamina. The tunnel may be drilled partly inside of a cricoid cartilage wall and partly on the outside of cricoid cartilage lamina.

In various alternative embodiments, an interface element may be positioned, implanted temporarily, implanted permanently, brought in place, inserted, and/or affixed. An interface element may include an electrode, a sensor, a catheter, a delivery device, a heat delivery device, a cold delivery device, a surgical device, a needle, a probe, a light transmission device, a tissue, a bulking material, light, heat, cold, fluid, drug, medicine, nutrient, radiation, or material. A laryngeal impairment may include unilateral vocal cord paralysis, bilateral vocal cord paralysis, dysphonia, dysphagia, and/or tendency of aspiration. A single interface element may be positioned unilaterally, multiple interface elements may be positioned unilaterally, or multiple interface elements may be positioned bilaterally. An interface element may be placed in communication with a controller that is implanted into the subject. A plurality of interface elements may be placed in communication with a controller that independently controls the interface elements, or each of a plurality of interface elements may be placed in communication with a separate controller such that each interface element is independently controlled by its respective controller.

In various alternative embodiments, certain aspects of the method may be performed in the surgical field of a neck incision and may be visually monitored intraoperatively, monitored intraoperatively by neural monitoring, monitored intraoperatively by monitoring of electromyographical signals, and/or performed endoscopically. Navigation of the interface element(s) and/or other implements may be performed using palpation, x-ray, CT, MRI, electrical test stimulators, a schablone manufactured according to general or the specific computer tomography data of the subject, a mask of the throat and mandible, and/or by use of a 2 or more dimensional video navigation system in relation to at least one of computer tomography, X-ray, MRI, and ultrasound data of the subject. Various elements may be repositioned, for example, with a different angle, a different direction, or a different starting point.

In various alternative embodiments, at least one laryngeal structure (e.g., a single vocal cord, both vocal cords, the epiglottis, or a pharyngeal constrictor) may be interfaced using the interface element(s), and the interface element(s) may be positioned for interfacing with a muscle, nerve, or receptor. Such interfacing may include, among other things stimulating a laryngeal structure, activating a laryngeal structure, blocking a laryngeal structure, inhibiting operation of a laryngeal structure, moving a laryngeal structure, removing a portion of a laryngeal structure, repairing a laryngeal structure, delivering a material to a laryngeal structure, or monitoring a laryngeal structure. Moving a laryngeal structure may include opening, closing, or varying tension of the laryngeal structure. The interfacing may include receiving and/or recording electromyographic signals of a related muscle and/or may include receiving and/or recording electroneurographic signals of a related nerve. In various alternative embodiments, various types of stimuli (e.g., electrical energy or drugs) may be delivered to a laryngeal structure via the interface element(s).

In certain embodiments, the interface element may include an electrode, in which case a portion of the electrode may be routed percutaneously through the skin to the outside of the subject and connected to an external stimulator for a certain duration to verify efficacy of the interfacing with laryngeal structures. In other embodiments, the interface element may include a sensor, in which case a portion of the sensor may be routed percutaneously through the skin to the outside of the subject and connected to an external recorder for a certain duration to verify efficacy of the interfacing with laryngeal structures. In yet other embodiments, the interface element may include a catheter, in which case a portion of the catheter may be routed percutaneously through the skin to the outside of the subject and connected to an external pump for a certain duration to verify efficacy of the interfacing with laryngeal structures. In some embodiments, the certain duration may be from 1 to 60 minutes. In other embodiments, the certain duration may be from 1 to 24 hours. In yet other embodiments, the certain duration may be from 1 to 7 days. In still other embodiments, the certain duration may be from 1 to 20 weeks. An interface element (e.g., an electrode, sensor, or catheter) may be permanently connected to a surgically implanted controller (e.g., a stimulator, recording device, or pump) in the case efficacy is proven or may be removed from the subject in the case efficacy has not been proven.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Figure 1:
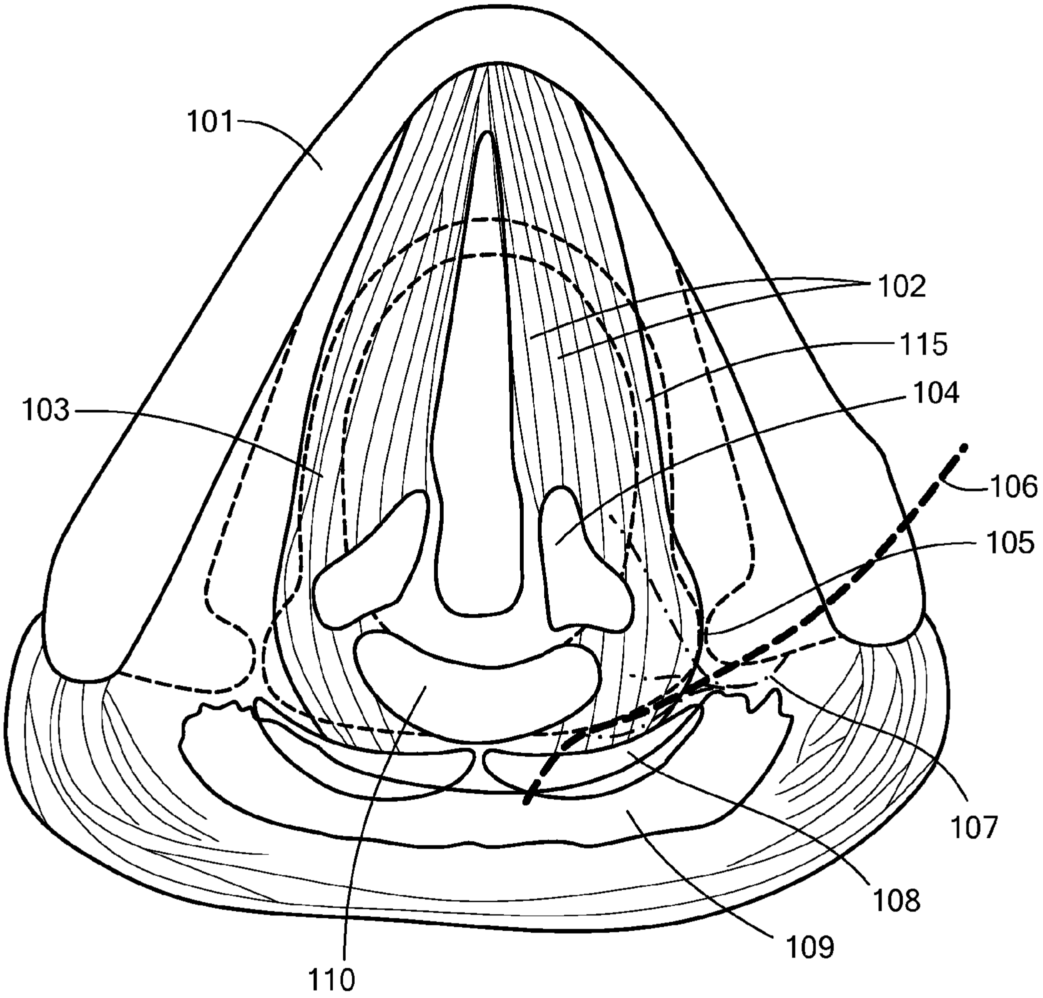
FIG. 1 shows a horizontal cut through the larynx and an insertion path for inserting an interface element into a space between PCA muscle and cricoid cartilage plate according to illustrative embodiments of the present invention.

Definitions. As used in this description and the accompanying claims, the following terms shall have the meanings indicated, unless the context otherwise requires:

A "subject" may be a human or animal.

An "interface element" is an element for directly or indirectly interfacing with the laryngeal structures of a subject and may include, but is in no way limited to, an electrode (e.g., for conveying electrical signals to and/or from an anatomical structure such as for stimulating, sensing, recording, etc.), a sensor (e.g., for monitoring an anatomical structure), a catheter (e.g., for conveying a fluid or other material to and/or from an anatomical structure), a delivery device (e.g., a pump or syringe for delivering a medication, drug, nutrient, fluid, or other material to an anatomical structure), a heat delivery device (e.g., a cauterization tool), a cold delivery device (e.g., a cryogenic tool), a surgical device (e.g., a scalpel or biopsy tool for removing tissue, a suturing device for repairing tissue, or other implement used in surgical procedures), a needle, a probe (e.g., for physical manipulation or stimulation of an anatomical structure), a light transmission device (e.g., a laser, optical fiber, scope, camera, light), a tissue, a bulking material, or other thing that can be delivered for interfacing with the laryngeal structures (e.g., light, heat, cold, fluid, drug, medicine, nutrient, radiation, or other material), to name but a few. An interface element may be used in conjunction with an integral or separate controller, such as a stimulation device (e.g., a pacer), a sensing device (e.g., a monitor), a recording device, and/or a manipulation device (e.g., a handle), to name but a few. In some cases, such a controller may be portable, wearable, and/or implantable. In some cases, such a controller may be capable of operating multiple interface elements either in unison or independently, e.g., for performing different functions on different laryngeal structures or for redundancy in case of a failure of an interface element or a component of the controller. In some cases, such a controller may be directly connected to an interface element (e.g., via a wire) or may interact with an interface element remotely (e.g., via a wireless communication interface). Thus, in various embodiments, multiple interface elements may be used with separate controllers, or multiple interface elements may be used with a single controller, and the interface elements may interact with the controller(s) in the same way or in different ways.

A "laryngeal structure" is a structure associated with the larynx, including, but not limited to, a single vocal cord, both vocal cords, the epiglottis, a pharyngeal constrictor, a supraglottic sphincter, or related structures (e.g., tissue, muscle, nerve, bone, cartilage), to name but a few.

In the context of the laryngeal structures of a subject, "unilaterally" means that an interface element is placed on one side of the body, vocal cord, or other structure (i.e., typically either the left side or the right side), and "bilaterally" means that an interface element is placed on each side of the body, vocal cord, or structure (i.e., typically both the left side and the right side). A "wing" is a part or aspect of the laryngeal structure.

A "needle" is an implement for forming a tunnel or for otherwise directly or indirectly positioning an interface element and may include, but is in no way limited to, a needle, a raspatorium, or a drill, to name but a few. In various embodiments, a needle may be solid or hollow, may be straight or bent in one or more places, and/or may be of fixed length or variable length (e.g., by telescoping).

A "thread" is used for directly or indirectly positioning an interface element and may include, but is in no way limited to, a thread, string, rope, chain, fiber, wire, filament, or tether, to name but a few.

"Repositioning" of a needle, interface element, or other thing and "re-generating" a tunnel may include changing the angle, direction, and/or starting point.

In certain contexts, terms such as "introducing," "positioning," "placing," and "inserting" may be used to refer to the same or similar operations, particularly with regard to forming a tunnel, inserting a thread, and/or positioning an interface element.

Embodiments of the present invention include endoscopically controlled, minimally invasive positioning of an interface element. The placement system and method reduce the risks related to a surgical procedure and at the same time allows an adjustment of stimulation to a laryngeal structure of the subject in vocalization, breathing or swallowing by alternatively stimulating opening, closing or elevation of the larynx. In addition, embodiments may allow more than one interface element to be inserted (e.g., bilaterally, or separate elements for opening and closing or larynx elevation). "Pull through" techniques may require special reinforcements of the interface element to accommodate traction stress. Pushing in the interface element under endoscopic view is an especially gentle method. Subperichondral or intra-chondral routing of the interface element may give better mechanical protection and electrical stimulation through the perichondrium, which may protect against corrosion of the interface element. Intra-operative endoscopic control and stimulation ensure optimal positioning of the interface element. Stimulation of opening and closing encourages a better preservation of movability of the crico-arytenoid joint and offers a better dynamic range potentially resulting in better exercise abilities and better speech quality in subjects than subjects without the stimulation. Bilateral interface element placement also offers the advantage of new three-dimensional electric dipole vectors for optimal stimulation, which may further improve the flexibility. Bilateral, separately controlled interface elements may also provide a higher safety in case of device failure. For example, if one side fails, the other side may (partially) compensate until the subject seeks clinical help.

Various exemplary embodiments are described with reference to the insertion of an electrode for facilitating the movement or stimulation of vocal cords. Other types of interface elements, however, may be used, in addition to, or lieu of, to facilitate interfacing with laryngeal structures generally according to various embodiments of the present invention.

In order to decrease current spread, the placement of electrodes preferably localizes current to a related anatomical structure (e.g., target muscle or nerve) as much as possible by a minimally invasive surgery. A needle insertion technique, instead of an open surgery, may provide the solution. In one embodiment, the capability of reaching a location or target (e.g., inside a subject's body) is provided by insertion of a curved needle system capable of going around corners, around obstacles and/or cartilage. In another embodiment, a straight path or tunnel may be used to reach the target or location.

Embodiments of the present invention also permit a minimally invasive, two stage implantation procedure to be possible. First, the interface element is inserted and a test stimulation session may be conducted over time, e.g., over several days or weeks, to show efficiency of the system. Then, when efficiency is positively verified a stimulator may also be implanted or when efficiency is not positively verified the interface element may be retracted out of the body without a complicated surgery.

Embodiments of the present invention are directed to the implantation of an interface element in the larynx using minimally invasive techniques. One embodiment includes straight tubular interface elements (e.g., electrodes) that may be used by inserting the elements in a "pull back" procedure after the interface element is attached to a thread that has been previously inserted along an insertion path.

Figure 2:
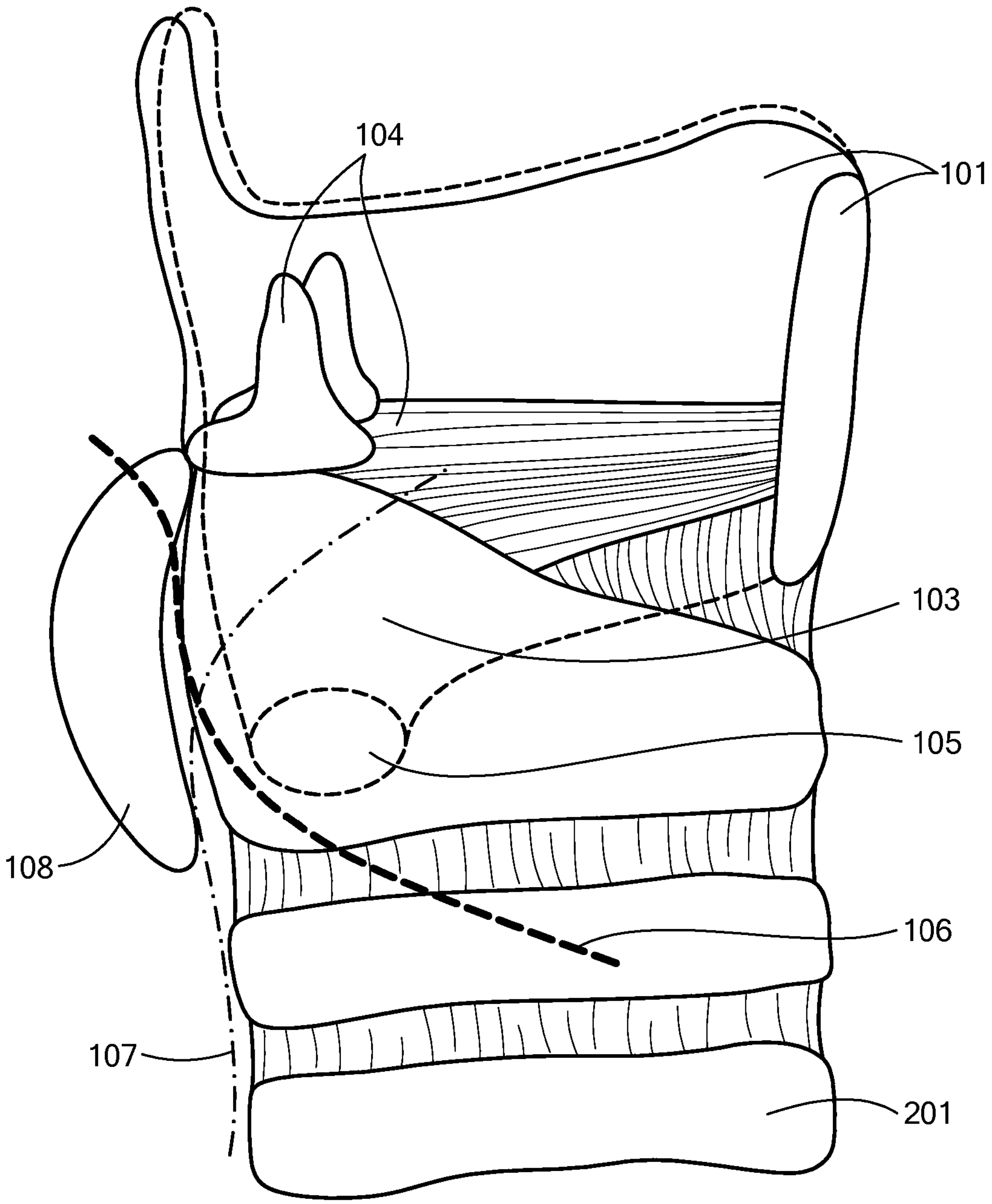
FIG. 2 shows a lateral view of the larynx and an insertion path for inserting an interface element into the space between the PCA muscle and the cricoid cartilage plate according to illustrative embodiments of the present invention.

FIG. 1 shows a horizontal cut through the larynx in the plane of the arytenoid cartilages. The projected way of the thread for inserting the interface element according to one specific embodiment is marked with a bold black interrupted line, insertion path 106. The discussion below explains how the interface element may be brought in the space between the PCA muscle 108 and the cricoid cartilage plate 110. In addition, the vicinity to the recurrent laryngeal nerve 107 and its medial branch is shown. FIG. 2 shows a lateral view of the larynx to illustrate how the thread for the pull back procedure may be directed ventrally below the larynx.

Under direct endoscopic laryngoscopic view, a slightly curved needle may be inserted into the backside of the larynx, called the postcricoidal region. The needle is inserted above the posterior cricoarytaenoid (PCA) muscle 108, which originates from the cricoid cartilage plate 110 and inserts at the arytenoid cartilage 104. The cricoid cartilage 115 includes a cricoid cartilage arch 103 and the cricoid cartilage plate 110, with the bottom of the cricoid cartilage 115 being the part on the anterior side of the vocal cord, the top of the cricoid cartilage 115 being the part on the posterior side of the vocal cord, and the two lateral parts or wings being on the left and on the right of the vocal cord. The PCA muscle 108 is the main and only opening muscle of the vocal cords 102. A branch of the recurrent laryngeal nerve 107 runs beneath it on the surface of the cricoid cartilage plate 110 from inferior lateral to superior medial. This nerve branch supplies the PCA muscle 108 with motor nerve fibers. The needle may be pushed laterally and downwardly towards the cricothyroid joint 105 in the subperichondral space on the posterior side of the cricoid cartilage plate 110. A tunnel may be preformed, e.g., with a raspatorium, in order to make this insertion easier. The needle may then be pushed out of the larynx in a more forward direction into the neck soft tissue. Attention should be paid to not penetrate the piriform sinus of the hypopharynx 109. Tracheal cartilage 201 is shown in FIG. 2 as a reference point.

The needle is thus held in the neck soft tissue. This is achieved through a small external surgical approach. The skin may be incised a few centimeters longitudinally or horizontally and laterally near the lower end of the larynx. The tissue between the larynx and the neck vessel sheath may be separated to create a space to find the needle and to protect the big neck vessels. In some cases, it may be helpful to rotate the larynx a little to the opposite side. Once the needle has been found, it is caught. A thread is fixed (e.g., knotted or by other connecting means) to the interface element tip and the needle. The needle is pulled back with the interface element connected to it by the thread. The interface element is then pulled in place. The interface element should to be strong enough to withstand the traction forces. The position of the interface element may be corrected or optimized by visually controlling the movement of the vocal cord 102 in response to stimulation, such as electrical stimulation. Once the best position has been established the interface element may be fixed with a suture to the side of the cricoid cartilage 115 or by other means. After a final control of electrical response, the thread may be cut at the surface of the mucous membrane on the back side of the larynx. The little pieces of thread that may be left at the electrode tip subsequently dissolve by themselves. A pacer housing may then be implanted via a small subcutaneous tunnel into a subcutaneous pocket, e.g., on the chest wall. A second incision on the chest wall to affix the pacer housing may be necessary. The incisions are closed with sutures or clips as well known to those skilled in the art. Enough time for wound healing is allowed before the device is used.

Alternatively, the needle may be pushed in a more downward direction so that it enters the neck in the space between the trachea and the esophagus. The advantages of this method are: 1) less tissue damage to the larynx and its connective tissue gliding space which is important for a good larynx elevation (during swallowing and speaking with different tone pitches), 2) the electrode tip is laying close to the cartilage surface which protects it from mechanical forces, 3) the electrode tip runs along the expected location of the nerve branches supplying the posterior arytenoid muscle, and 4) more laterally, the nerve stem or other branches of the recurrent laryngeal nerve come close to the multi-electrode so that the electrode may be used for opening and closing the vocal cord.

Figure 3:
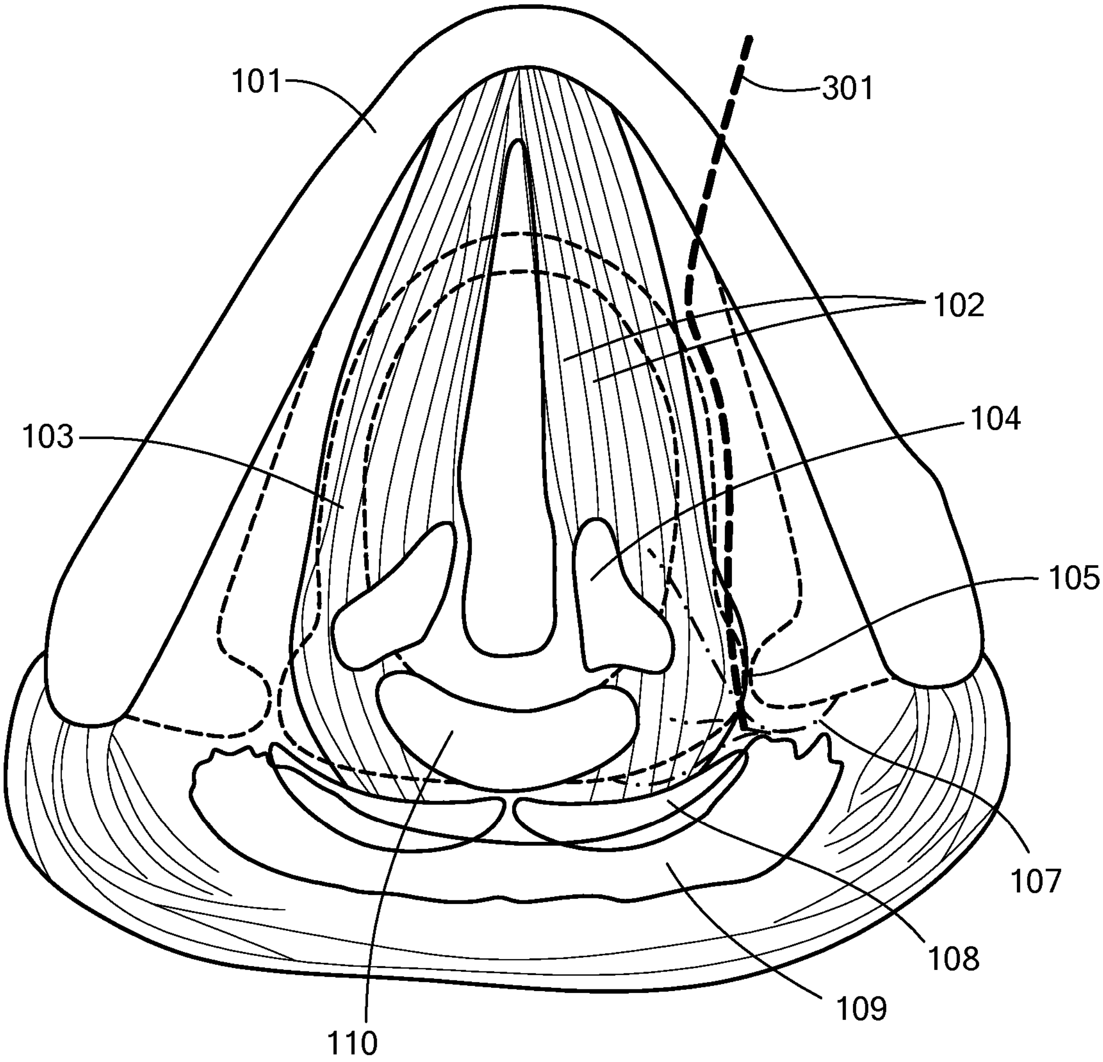
FIG. 3 shows a horizontal cut through the larynx and an insertion path for inserting an interface element into a subperichondral tunnel according to illustrative embodiments of the present invention.
Figure 4:
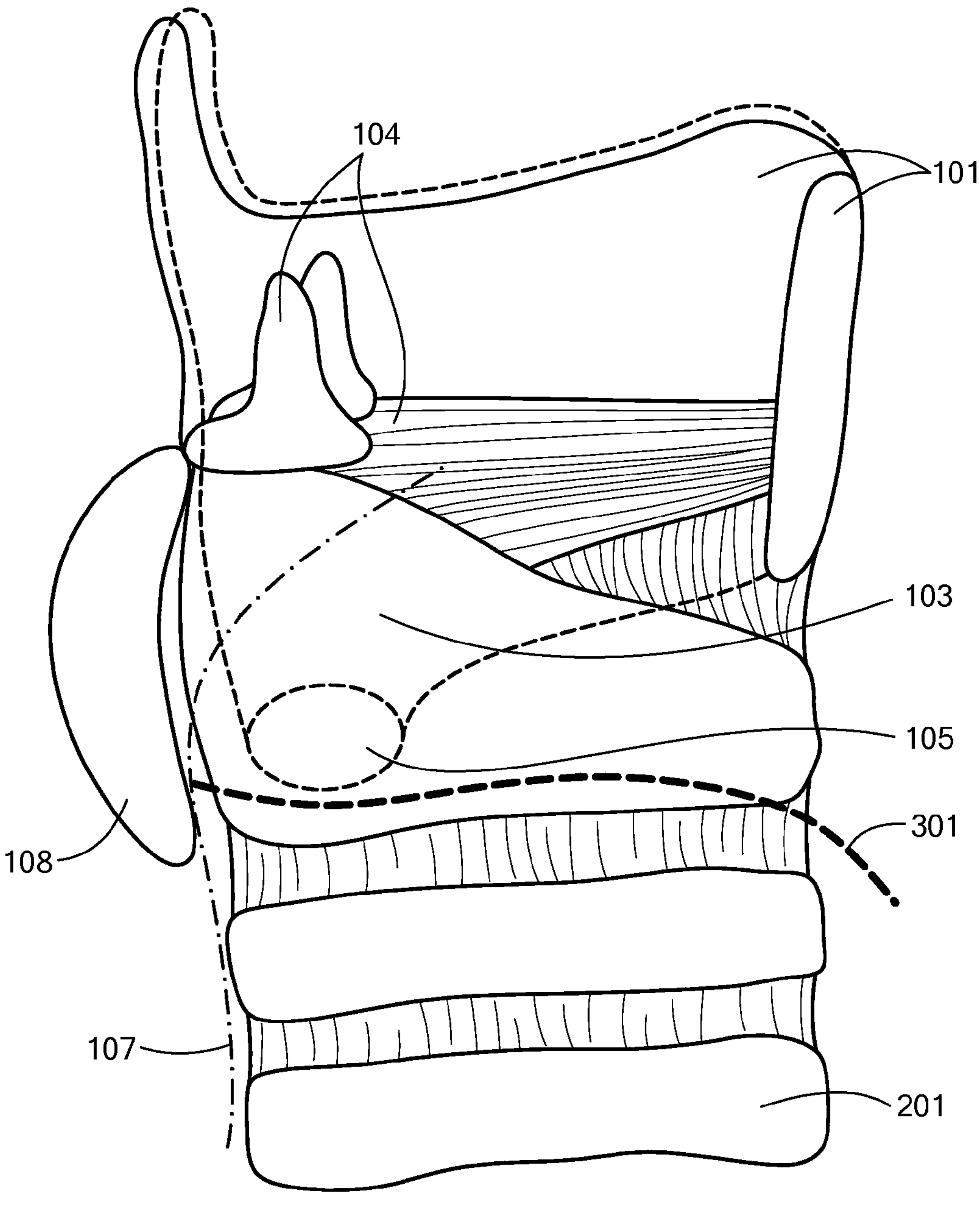
FIG. 4 shows a lateral view of the larynx and the insertion path for an interface element inserted into the subperichondral tunnel according to illustrative embodiments of the present invention.

One embodiment may be an interface element inserted into a subperichondral tunnel on the outside of the cricoid cartilage arch 103, through a tunnel through the cricoid cartilage arch 103 to the posterior subperichondral space of the cricoid cartilage plate 110, or with the help of a needle through the cricoid cartilage 115 to the posterior subperichondral space of the cricoid cartilage plate 110. FIG. 3 shows an interface element inserted into a subperichondral tunnel, insertion path 301 and FIG. 11 (to be described in more detail below) shows an interface element inserted through the cricoid cartilage 115. As shown, the tip of the electrode reaches behind the cricothyroid joint 105 where the recurrent laryngeal nerve 107 divides into its branches. FIG. 4 shows a lateral view of the electrode inserted into the subperichondral tunnel.

Figure 5:
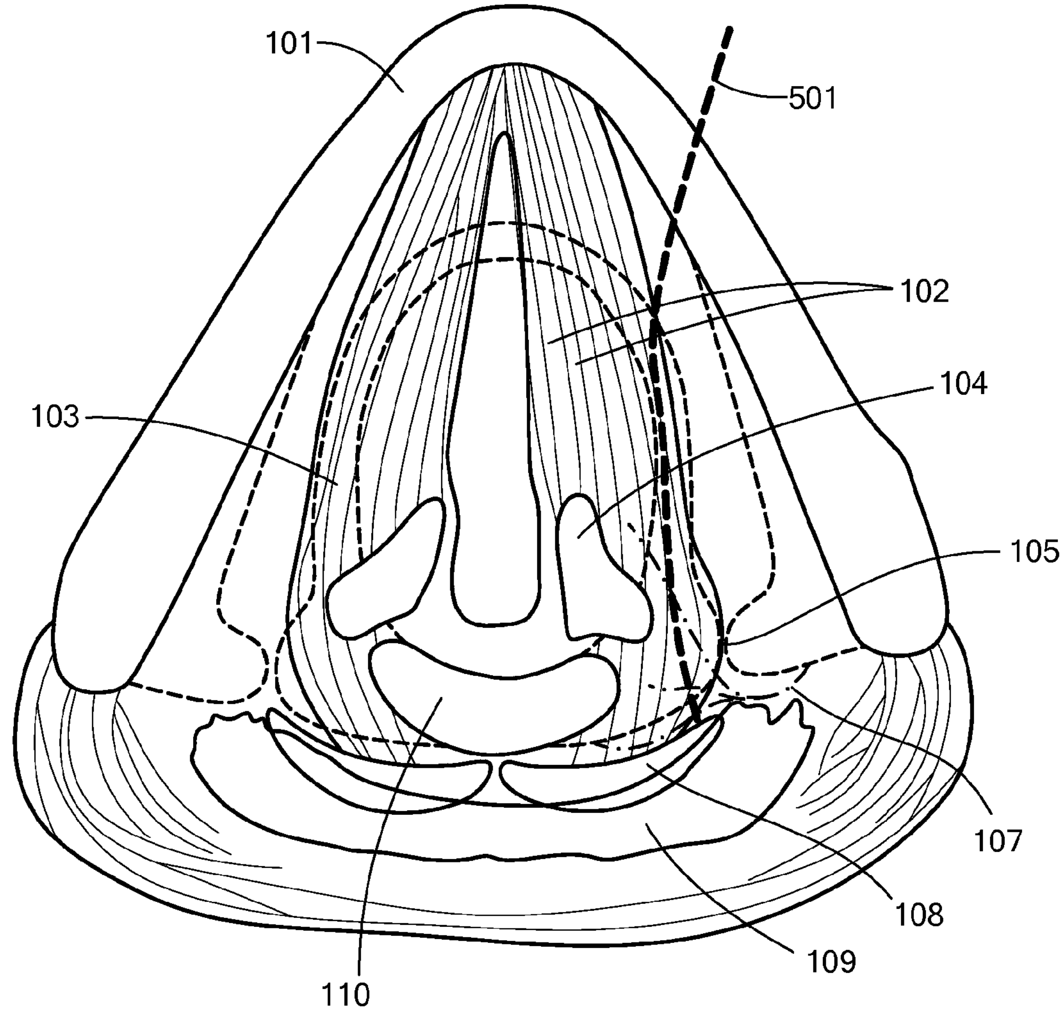
FIG. 5 shows a horizontal cut through the larynx and an insertion path for inserting an interface element into a drill hole through cricoid cartilage according to illustrative embodiments of the present invention.
Figure 6:
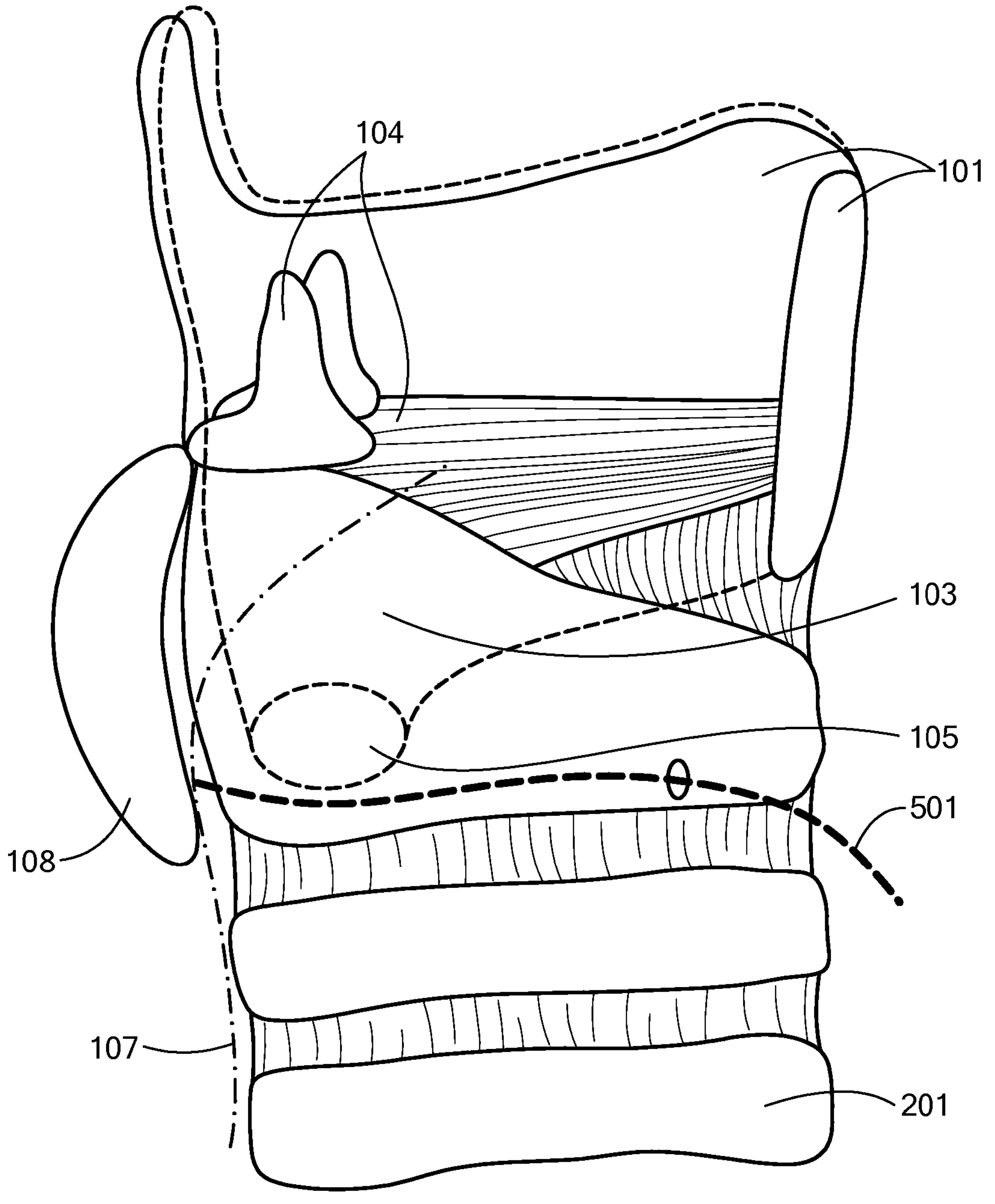
FIG. 6 shows a lateral view of the larynx and the insertion path for inserting an interface element into a drill hole through the cricoid cartilage according to illustrative embodiments of the present invention.

Similarly, FIGS. 5 and 6 show an interface element inserted into a tunnel through the cricoid cartilage 115. The tunnel may be straight or bent according to the technology used to generate the tunnel. It may be possible to reach the recurrent laryngeal nerve 107 more medially and therefore better stimulate the opening movement of the vocal cord 102. The skin may be incised a few centimeters longitudinally or horizontally and laterally near the lower end of the larynx where the cricoid cartilage 115 is or the skin may not even be incised and the needle is directly pushed through the skin.

After dissection of subcutaneous tissue the prelaryngeal "strap muscles" have to be moved medially or laterally. The upper end of the thyroid gland often covers the cricoid cartilage arch 103. It is dissected from the cartilage to expose the cricoid cartilage arch 103. This is usually easily achieved, but care should be taken not to damage any nerve structures. In some cases, a vessel may have to be tied. Once the cricoid cartilage arch 103 with anterior thyrocricoid muscle sitting on it is exposed, the larynx is slightly turned to the opposite site. The perichondrium of the cricoid cartilage 115 is incised. A subperichondral tunnel may be formed with a small curved raspatorium. The tunnel may be progressed towards the cricothyroid joint 105 and extended a little further either above or below it. The cricothyroid joint 105 may be identified by palpation or by other means.

The stimulating electrode may be inserted into this tunnel. This may be achieved with an electrode which is stiff enough by itself or which is otherwise stabilized. Small hooks and/or a miniature endoscope like in sialography (endoscopic examination of saliva ducts) or a tube that may be split and fits the electrode in its lumen may be used to aid insertion. The correct positioning of the electrode may be controlled by laryngoscopic control of vocal cord movements. Once the best position has been established the electrode may be fixed with a suture, silicone anchors or another kind of fixation to the side of the cricoid cartilage 115. Small tags on the electrode lead may be used to achieve a good fixation.

A pacermaker may then be implanted via a small subcutaneous tunnel into a subcutaneous pocket, e.g., on the chest wall. A second incision on the chest wall to affix the pacermaker may be necessary. The incisions are closed with sutures or clips as well known to those skilled in the art. Enough time for wound healing is allowed before the device is used.

Alternatively, the interface element may be routed through a tunnel (e.g., in the form of a drill hole) through the arch of the cricoid cartilage 103 itself towards the backside of the cricoid cartilage plate 110. This would allow a lightly more medial position of the electrode tip and make it easier to stimulate the nerve branches to the PCA muscle 108. For example, an electrode may be inside a needle during an insertion, fixed inside the needle and then pushed out or held in place while the needle is pulled back, or the tip may be bent around the edges of the tip of the needle like a "hooked-wire" electrode and, thus, is self-fixing when pulling the needle back, or the electrode may not be inside the needle during insertion but pulled inside after the needle has been placed and then pushed out or held in place while the needle is pulled back. The advantages of this embodiment are: 1) reduced tissue damage to the larynx and its connective tissue gliding space which is important for a good larynx elevation (during swallowing and speaking with different tone pitches) and 2) the electrode tip is laying close to the cartilage surface or inside the cartilage which protects it from mechanical forces.

The navigation for the insertion path or route may be done by the help of landmarks only, or by the assistance of a template manufactured according to general or the specific computer tomography data of the subject, or by the assistance of a mask of throat and mandible comparable to radiation masks, or with a three or more dimensional video navigation system in relation to the computer tomography, X-ray, MRI or ultrasound data of the subject. When the needle is pushed through the cartilage and exits on the backside of the cartilage or the electrode is inside the needle with the tip of the electrode extending slightly beyond the needle tip, the needle may then be connected to an electrical stimulation apparatus to verify the position of the needle tip by the effectiveness of the vocal cord opening evoked by the electrical stimulation. The needle may be insulated in selected areas (e.g., insulated except for the tip) or may not be insulated at all. If the effectiveness of the vocal cord opening is not satisfactory, the needle may be pulled back and pushed through the cartilage again at another angle till the needle leaves the cartilage on the other side and is pushed out in a certain position between posterior cricoarytenoid muscle and cricoid cartilage. The process of verifying the position of the needle tip may then be repeated. For example, the needle or the electrode inside the needle with the tip of the electrode extending slightly beyond the needle tip may then be connected to an electrical stimulation apparatus to verify the position of the needle tip by the effectiveness of the vocal cord opening evoked by the electrical stimulation and so on.

Figure 7:
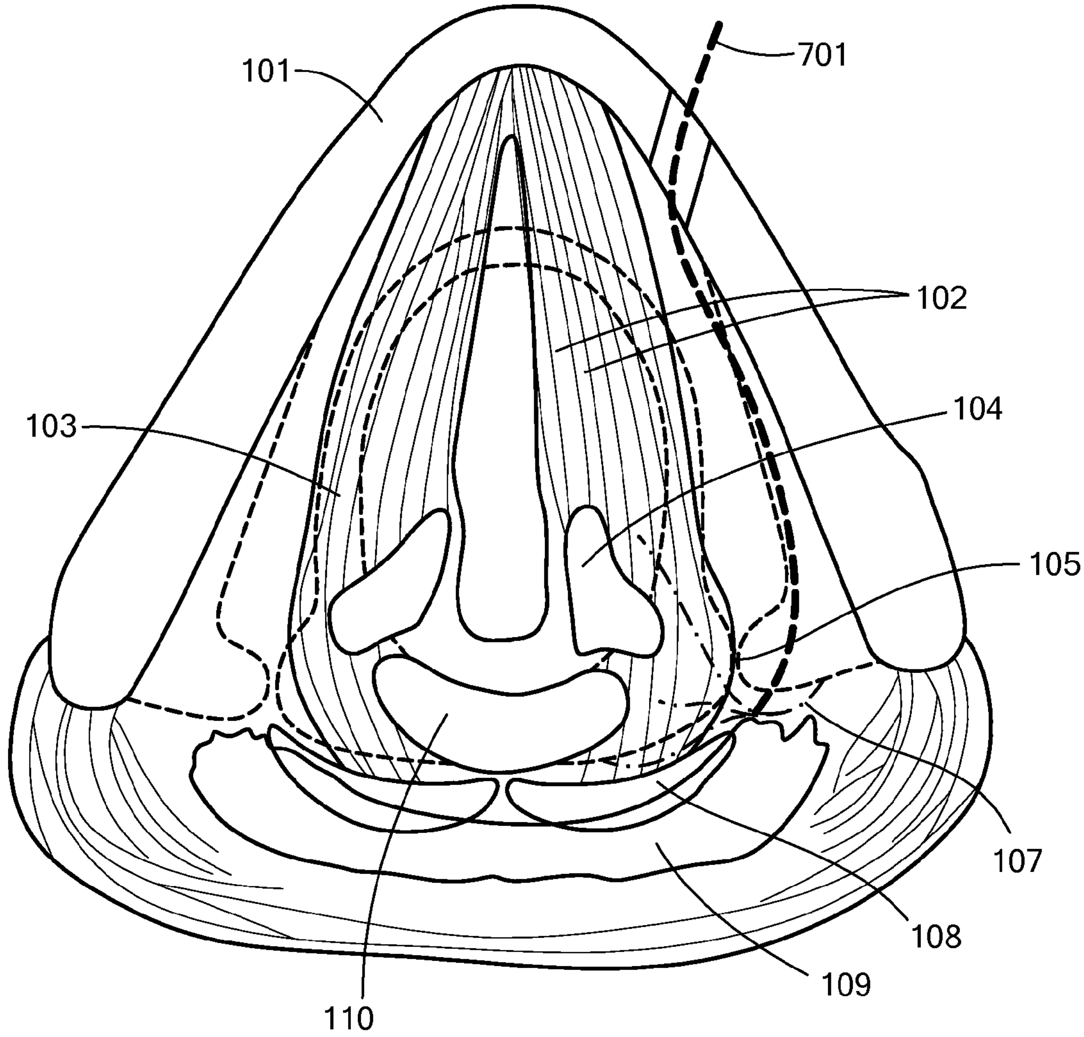
FIG. 7 shows a horizontal cut through the larynx and an insertion path for inserting an interface element into a subperichondral tunnel on an inside of thyroid cartilage lamina according to illustrative embodiments of the present invention.
Figure 8:
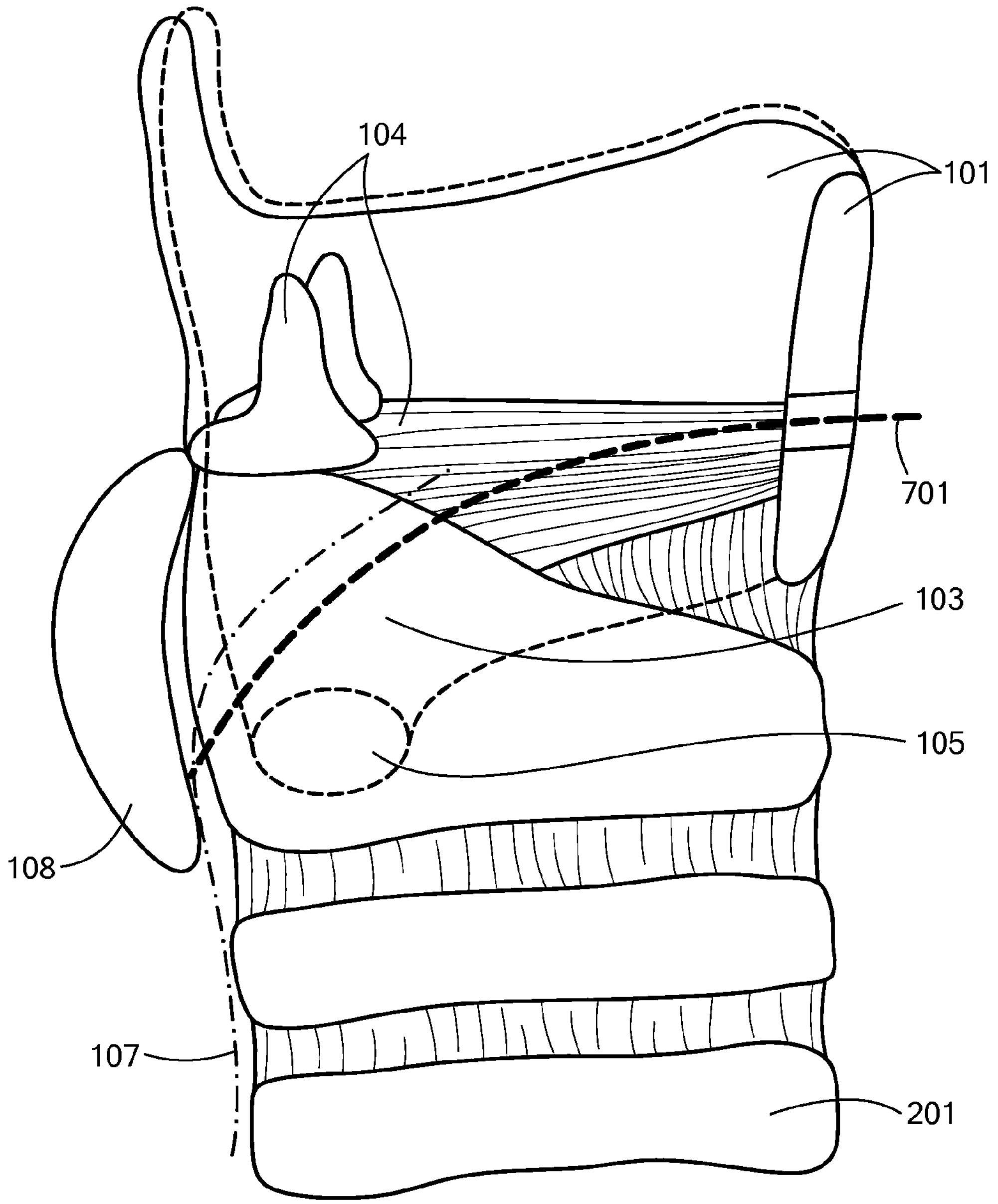
FIG. 8 shows a lateral view of the larynx and an insertion path for inserting an interface element into the subperichondral tunnel on the inside of the thyroid cartilage lamina according to illustrative embodiments of the present invention.

One embodiment may use straight tubular electrodes inserted into a tunnel on the inside of the thyroid cartilage. FIG. 7 shows an electrode insertion into a subperichondral tunnel on the inside of the thyroid cartilage lamina, insertion path 701. FIG. 8 shows the lateral view. As shown in FIGS. 7 and 8, the tunnel declines a little to reach the dividing region of the recurrent laryngeal nerve 107. It may not be necessary in all cases to have the electrode reach as far as the dividing point of the recurrent laryngeal nerve 107.

A small, preferably horizontal, prelaryngeal skin incision in the neck may be made. The thyroid cartilage 101 may be exposed in the anterior part. A tunnel may be made (e.g., by drilling a hole) preferably half way between the superior and inferior thyroid incisures (which is about the height of the glottic plane) in the anterior third of the cartilage. The tunnel may be large enough to enter with a small raspatorium, a curved needle (e.g., a curved needle system or a telescopic curved needle system), or some other tool to create a subperichondral tunnel at the inside of the thyroid cartilage 101. The tunnel may be made slightly downwards in the direction of the cricothyroid joint 105. It extends either above or below the joint into the region of the recurrent laryngeal nerve 107 and its dividing point. Finding the way towards the recurrent laryngeal nerve 107 near the cricothyroid joint 105 may be navigated by palpation, x-ray, CT/MRI-navigation or the use of electrical test stimulators. In some cases, the tunnel may not progress as far as the joint region if only the anterior branch is stimulated (for adduction of the vocal cord).

Into this tunnel, the stimulating electrode may be inserted. This may be achieved with an electrode which is stiff enough by itself or has been otherwise stabilized. Small hooks and/or a miniature endoscope like in sialography (endoscopic examination of saliva ducts) or a tube that may be split and fits the electrode in its lumen may be used to aid insertion. The correct positioning of the electrode may be controlled by visual control of larynx movements. Once the desired position has been established the electrode may be fixed near the tunnel with a suture or by other means. A pacermaker may then be implanted via a small subcutaneous tunnel into a subcutaneous pocket, e.g., on the chest wall. A second incision on the chest wall to affix the pacermaker may be necessary. The incisions may be closed with sutures or clips as well known to those skilled in the art. Enough time for wound healing is allowed before the device is used. Alternatively, or in addition, the insertion path or a second insertion path may be advanced more cranially. An electrode may be placed there to stimulate the supraglottic sphincters (muscles closing the larynx entrance, protection against food/foreign body aspiration). Different electrodes may be inserted for the vocal cord(s) and for the supraglottic sphincters.

The advantages of this embodiment are: 1) reduced tissue damage to the larynx and its connective tissue gliding space which is important for a good larynx elevation (during swallowing and speaking with different tone pitches). 2) the electrode tip is laying close to the cartilage surface beneath the perichondrium which may protect it from mechanical forces. The perichondrium is conductive for electrical currents and probably prevents a sheathing of the electrode with excessive connective tissue which "insulates" the electrode (e.g., increasing the electrical resistance and therefore the energy drain from the stimulation device to maintain a constant stimulus effect). Also, corrosion of the electrode may be reduced. 3) multiple electrodes may reach the nerve branches to the internal thyroarytenoid muscle or the muscle itself and at its tip the branching point of the recurrent laryngeal nerve. The electrode may, therefore, stimulate closing of the glottic gap, and enhancing the tension of the vocal cord as well as opening the glottic gap by stimulating the nerve branches to the posterior cricoarytenoid muscle.

Figure 9:
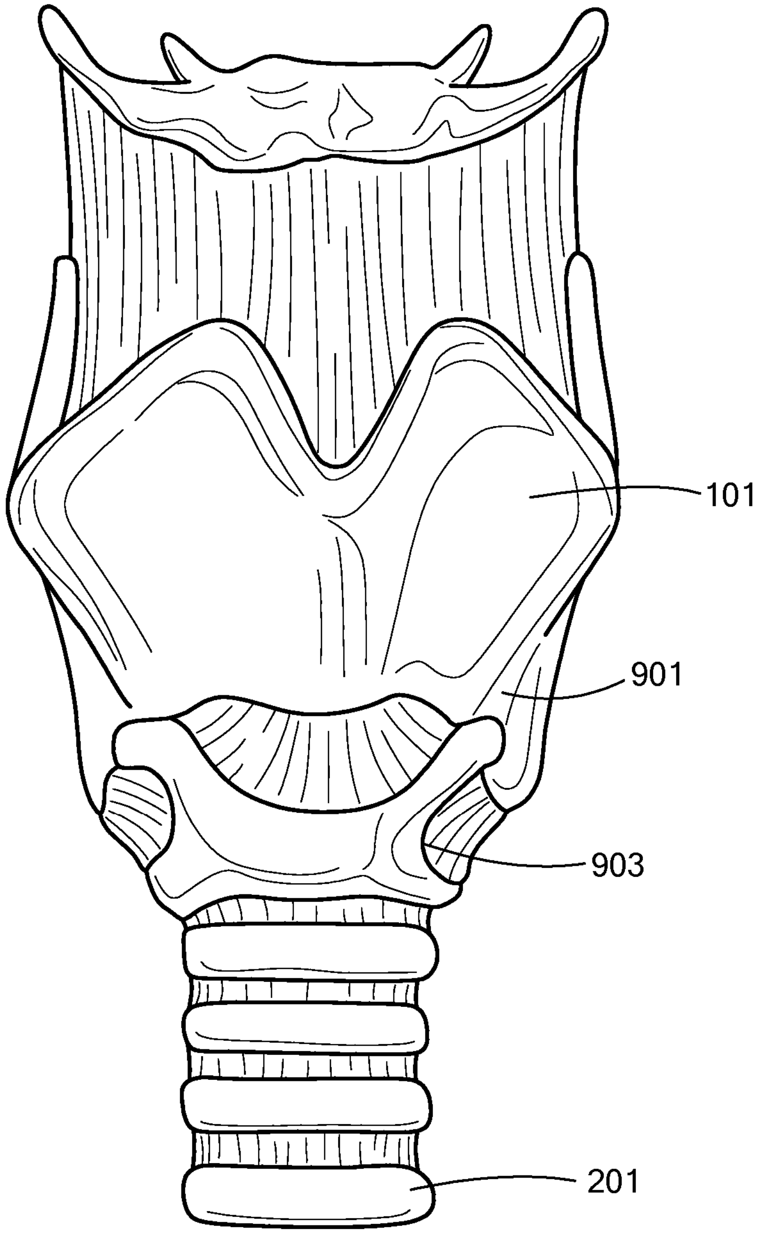
FIG. 9 shows a front view of the larynx and the tuberculum thyroideum caudale as a landmark of the starting point of the insertion according to illustrative embodiments of the invention.

Another embodiment may use a straight insertion path or tunnel for inserting an interface element into an insertion route through the cricoid cartilage. As shown in FIG. 9, the starting point of the insertion path 903 may be near the tuberculum thyroideum caudale 901, which may be used as a landmark. The insertion point may start about a few millimeters in front or about up to 2 cm backward. Due to the varying thickness of the cricoid cartilage 115, the height may not be varied substantially in various embodiments.

Figure 10:
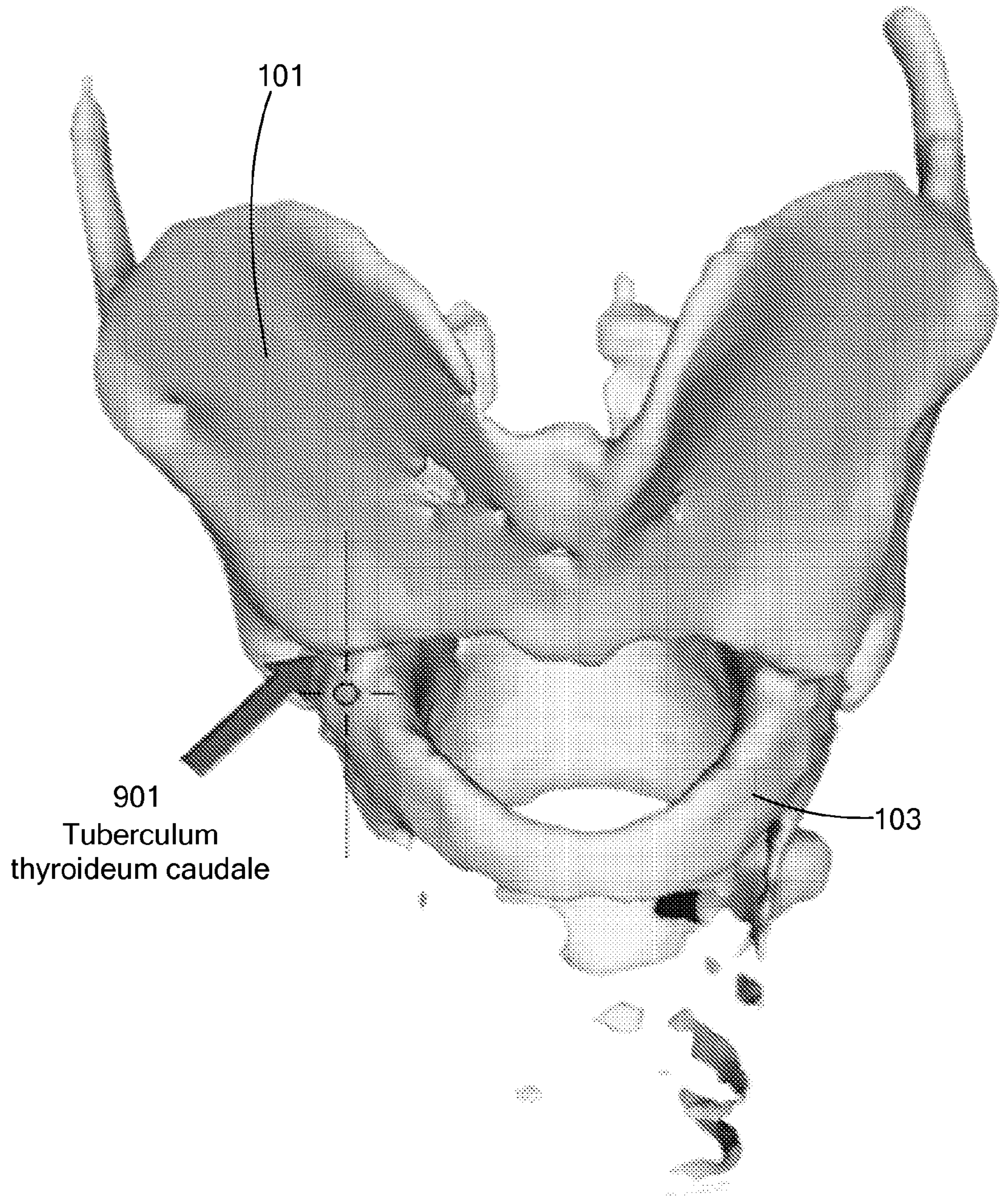
FIG. 10 shows a 3-dimensional computer tomography reconstruction of the vocal cord that includes the tuberculum thyroideum caudale according to illustrative embodiments of the invention.
Figure 11:
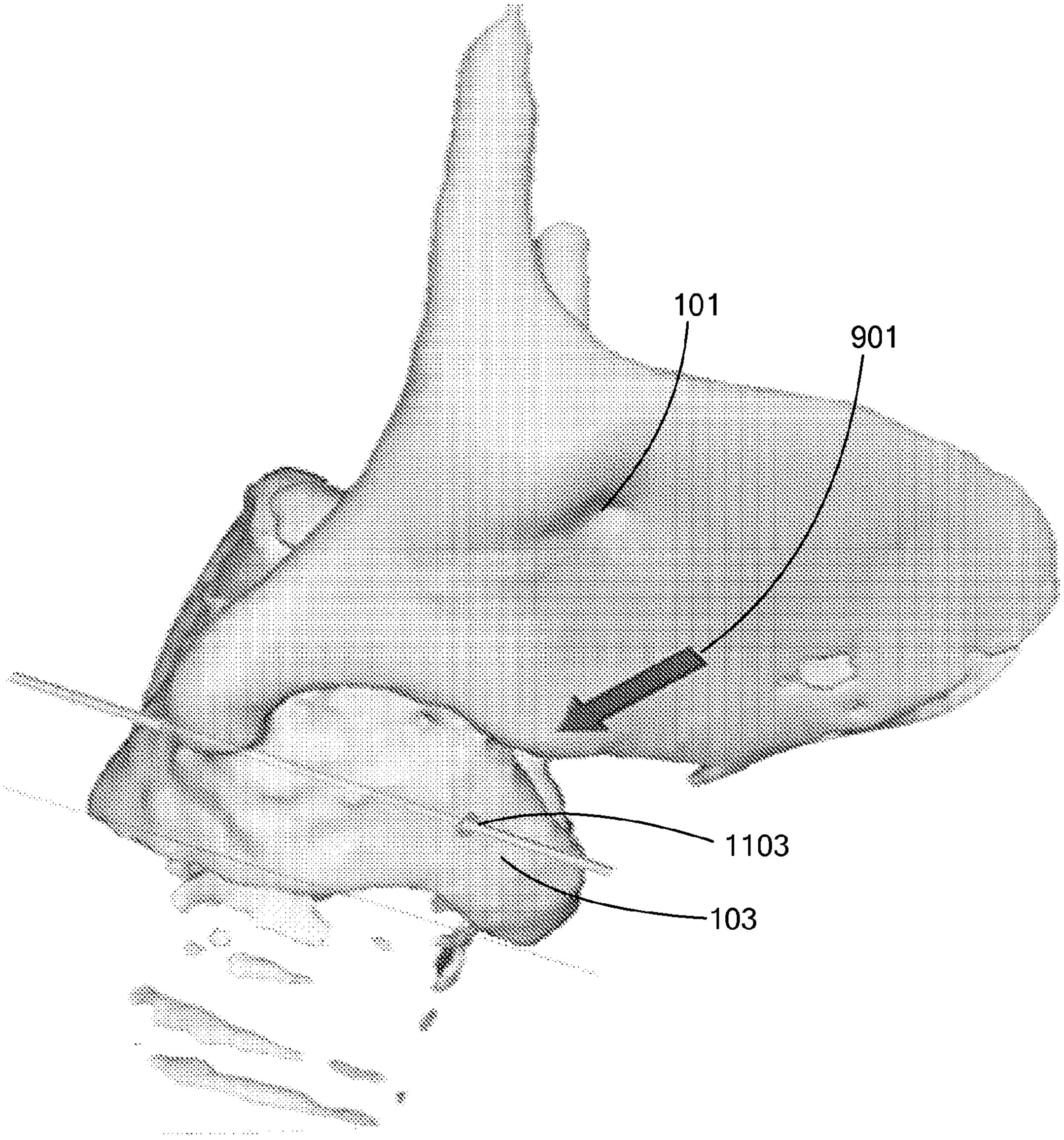
FIG. 11 shows a lateral view of a 3-dimensional computer tomography reconstruction of the vocal cord and the insertion path for inserting an interface element into an insertion route through the cricoid cartilage according to illustrative embodiments of the present invention.
Figure 12:
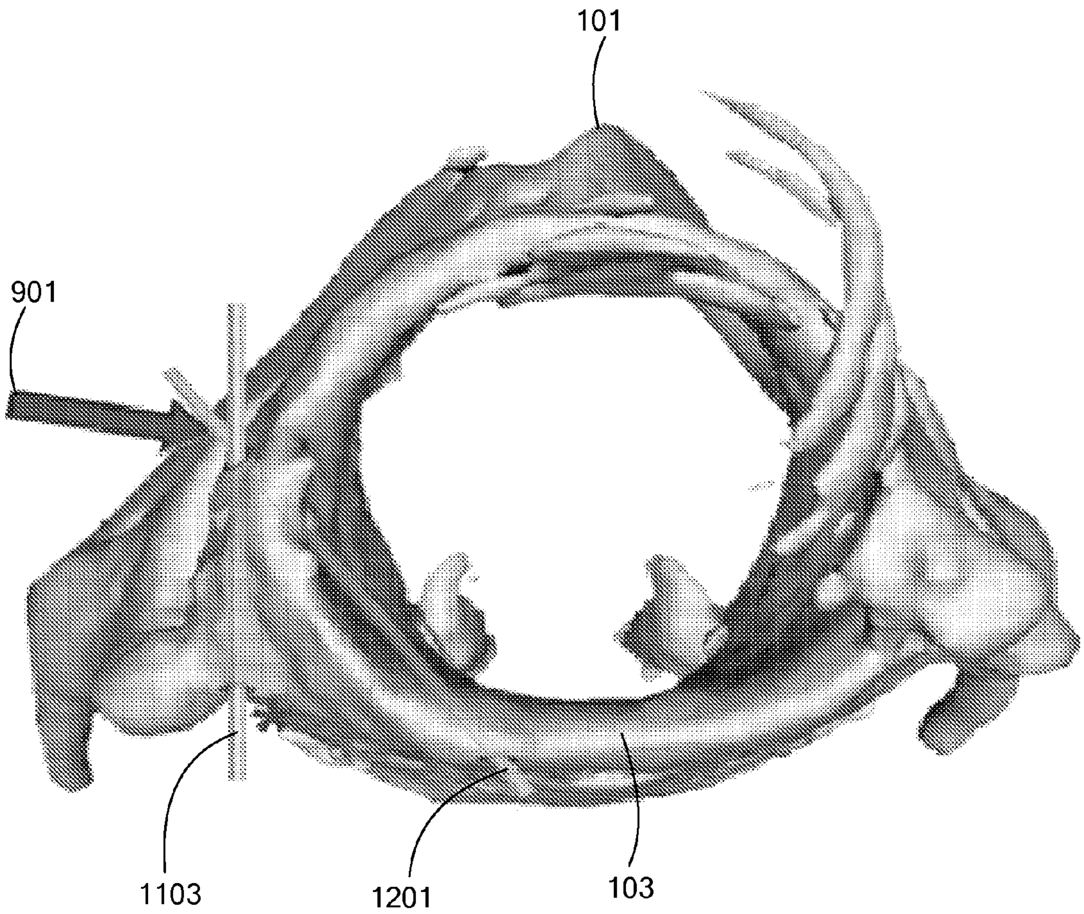
FIG. 12 shows a 3-dimensional computer tomography reconstruction of the vocal cord from below illustrating the cricoids cartilage arch thickness towards the cricoids cartilage plate according to illustrative embodiments of the invention.

FIG. 10 shows a front perspective view and FIG. 11 shows a lateral view of a 3-dimensional computer tomography reconstruction of the vocal cord that includes the tuberculum thyroideum caudale 901, which is marked by an arrow. FIG. 12 shows a 3-dimensional computer tomography reconstruction of the vocal cord from below illustrating the cricoid cartilage arch 103 thickness towards the cricoid cartilage plate 110. Because the lateral walls of cricoid cartilage 115 are thickened at a particular height, it is possible to reach almost midline even with a straight insertion route by beginning the insertion near or at the tuberculum thyroideum caudale 901. One insertion path may include a straight tunnel 1201 and another insertion path may include a saggital tunnel 1103 (also marked with an asterick), which ends about below the recurrent laryngeal nerve (RLN). Thus, a needle may be inserted in a straight line through one or both of the lateral walls of the cricoid cartilage 115 in a direction to reach the nerve branches of the recurrent laryngeal nerve 107 which innervate the PCA muscle 108. At other heights of the cricoid cartilage 115 (with less thickness), an angled or curved insertion route may be used along the inner and outer borders of the lateral walls of the cricoid cartilage 115 to stay inside the walls. Therefore, the route of the needle may start to enter the cricoid cartilage 115 right after passing through the skin and may stay inside the lateral wall till the needle leaves the backside of the cricoid cartilage 115 directly near a branch of the recurrent laryngeal nerve 107 innervating the PCA muscle 108.

Figure 13:
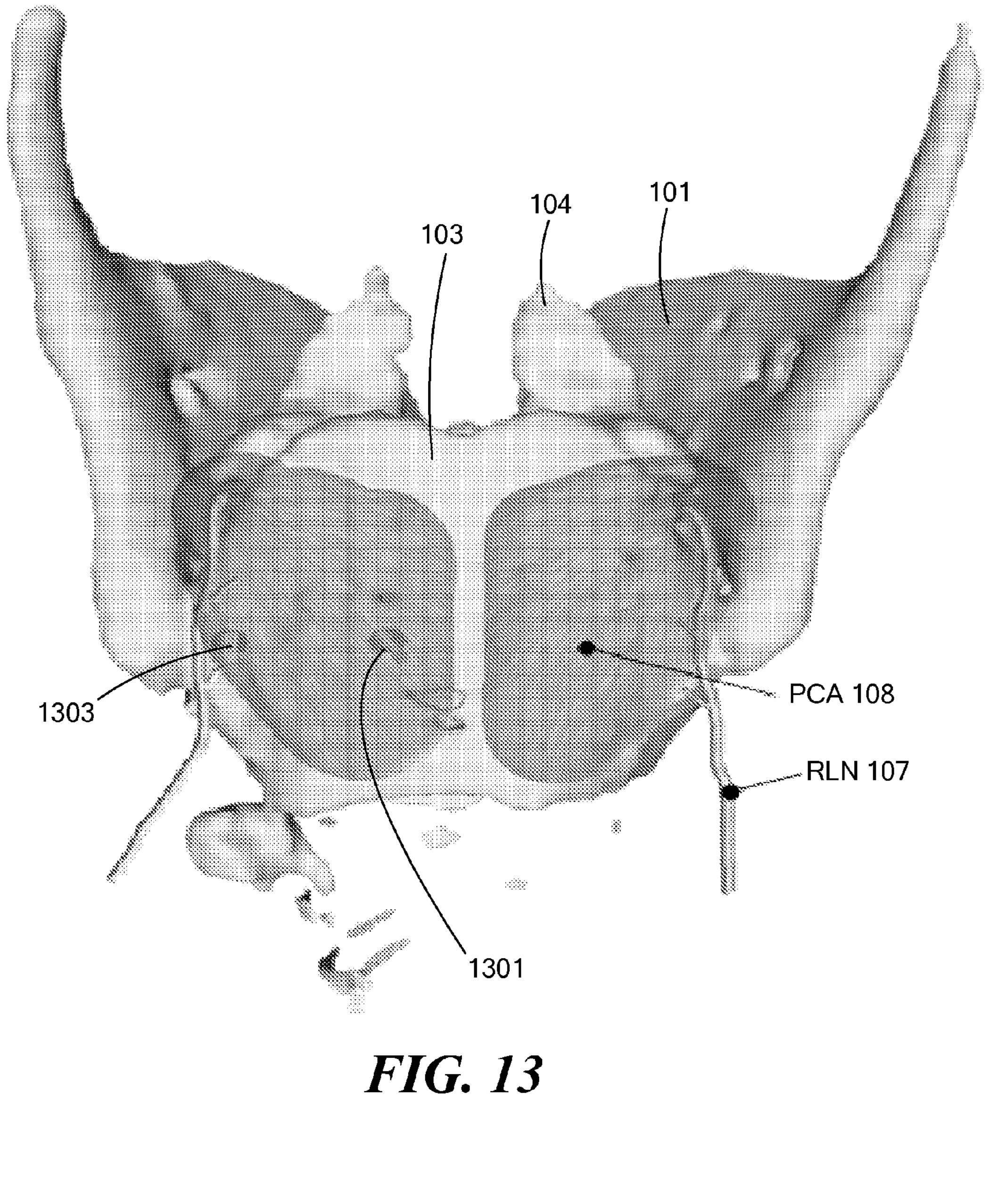
FIG. 13 shows a 3-dimensional computer tomography reconstruction of the vocal cord from behind illustrating the exit point of the insertion route through the crycoid cartilage appearing under the posterior cricoarytenoid muscle according to illustrative embodiments of the invention.
Figure 14:
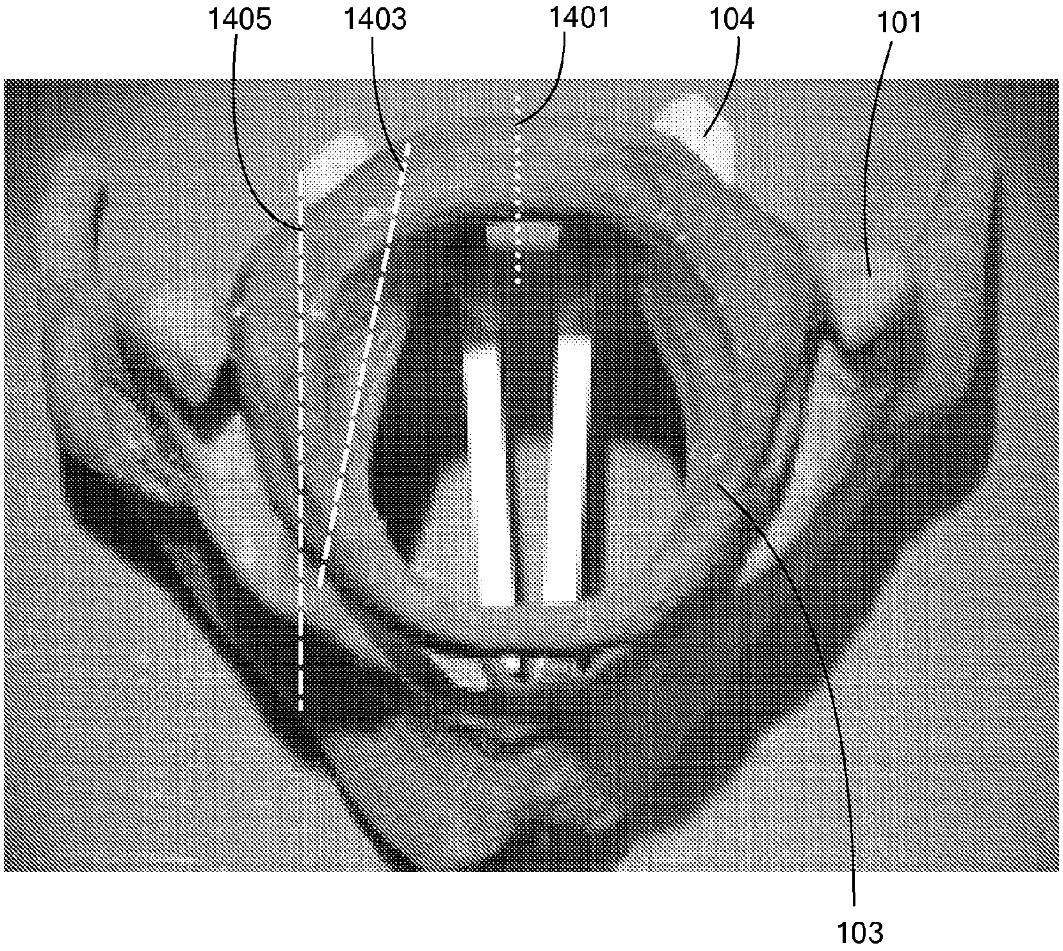
FIG. 14 shows a 3-dimensional computer tomography model of the vocal cord photographed from below illustrating that the cricoid cartilage arch thickens towards the cricoid cartilage plate according to illustrative embodiments of the invention.
Figure 15:
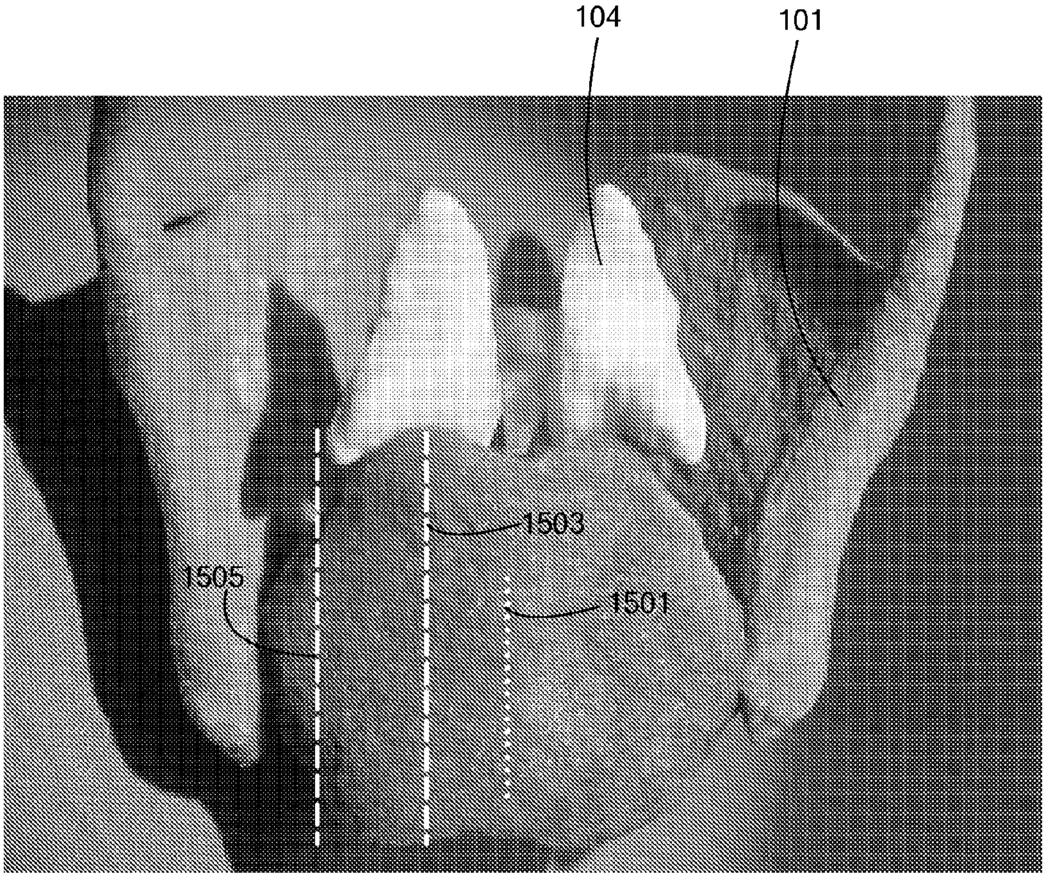
FIG. 15 shows a 3-dimensional computer tomography model of the vocal cord photographed from behind according to illustrative embodiments of the invention.

FIG. 13 shows a 3-dimensional computer tomography reconstruction of the vocal cord from behind illustrating the exit point 1301 and 1303 of the insertion route through the crycoid cartilage 103, 110 appearing under the PCA muscle 108. Exit point 1301 shows where the straight tunnel 1201 (shown in FIG. 12) exits and exit point 1303 shows where the saggital tunnel 1203 (shown in FIG. 12) exits. FIG. 14 shows a 3-dimensional computer tomography model of the vocal cord photographed from below illustrating that the cricoid cartilage arch thickens towards the cricoid cartilage plate. Due to the thickness, it is possible to reach almost midline 1401 with a straight tunnel 1403 or a saggital tunnel 1405 ending about below the recurrent laryngeal nerve (RLN). FIG. 15 shows a 3-dimensional computer tomography model of the vocal cord photographed from behind. As shown, the midline 1501, the medial direction 1503 of a tunnel, and the lateral direction 1505 of a tunnel are marked with white dotted lines.

Figure 18:
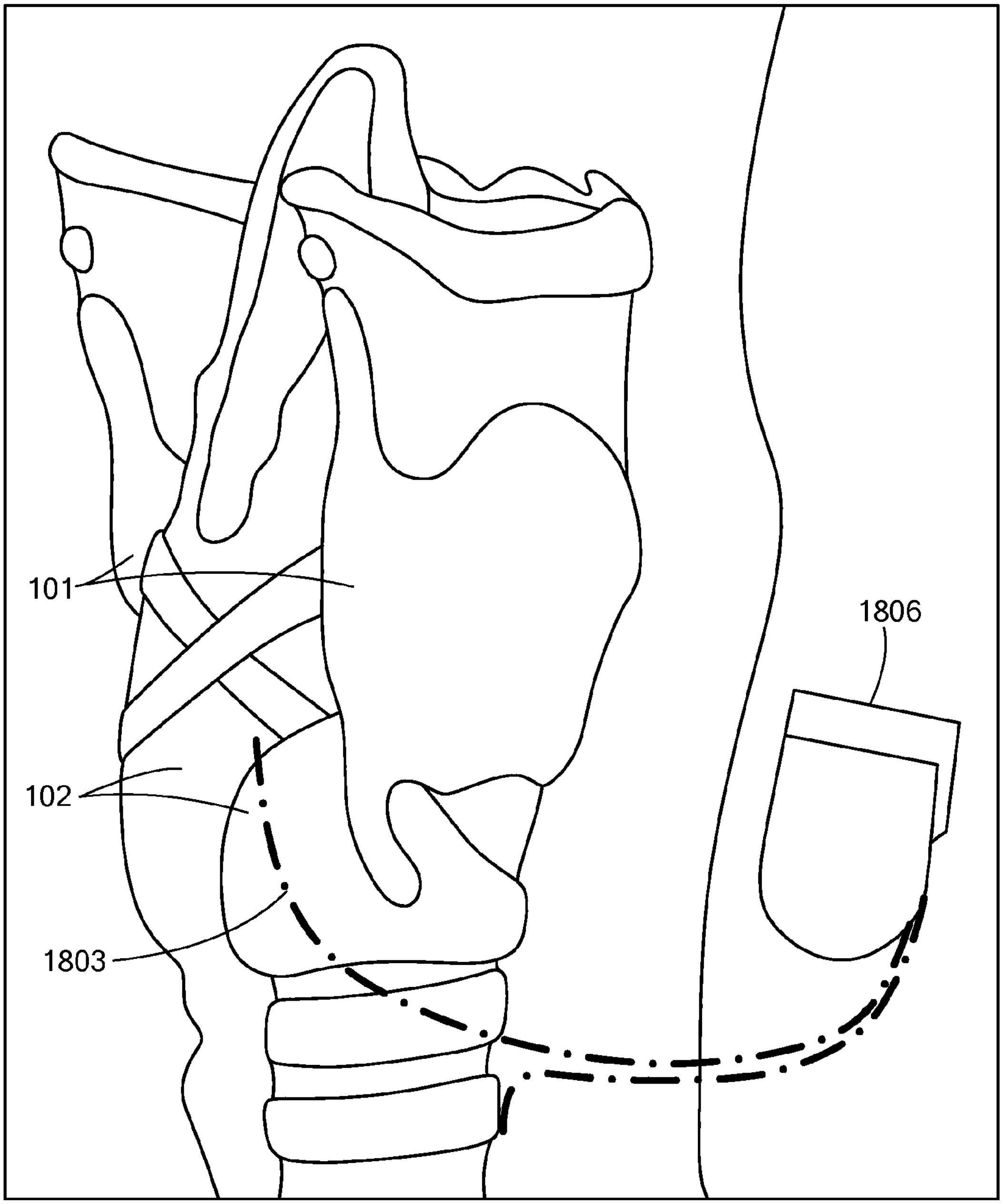
FIG. 18 shows a lateral view of the larynx and an insertion path for inserting an interface element between muscle and cartilage according to illustrative embodiments of the present invention.

FIG. 18 shows a lateral view of the larynx and an insertion path or tunnel for inserting an interface element 1803 between muscle and cartilage. The interface element 1803 may be connected to a pacemaker or stimulator 1806, which may be implanted via a small subcutaneous tunnel into a subcutaneous pocket on the subject.

Figure 16B:
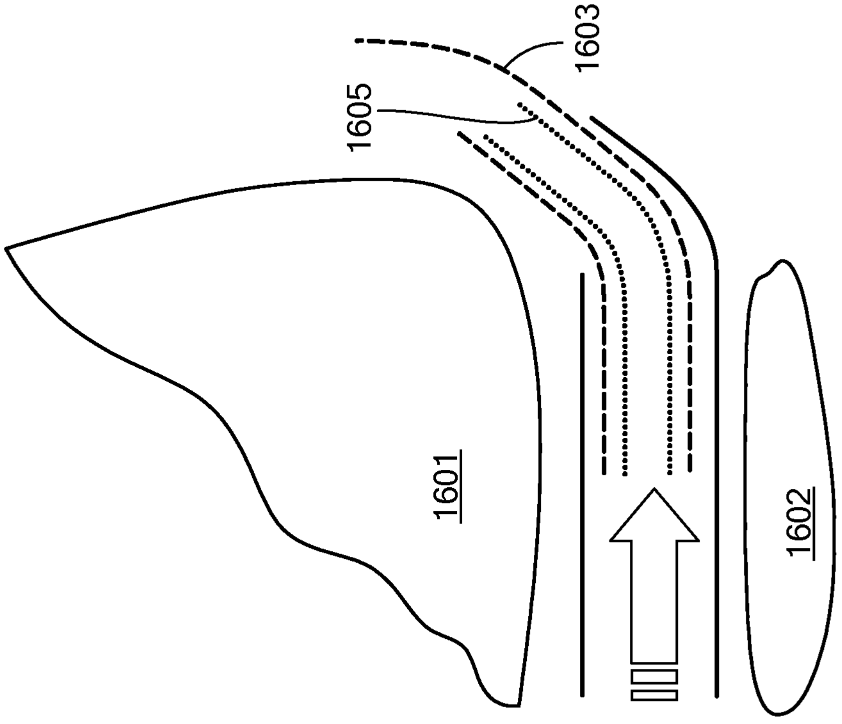
FIGS. 16A-M show an interface element insertion system having a curved needle system and an insertion path between muscle and cartilage according to illustrative embodiments of the present invention.
Figure 16A:
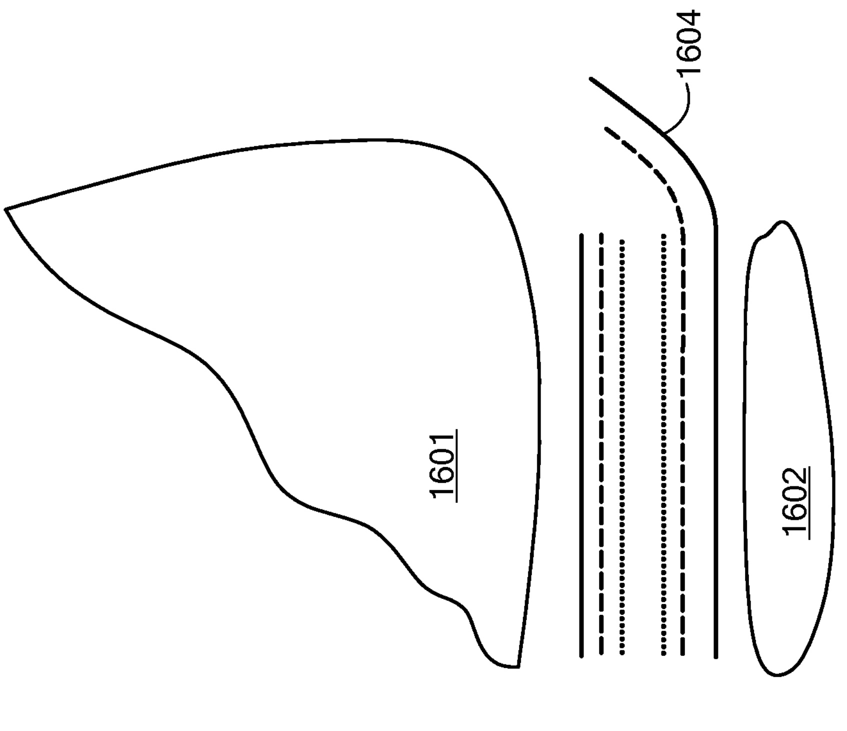
Figure 16C:
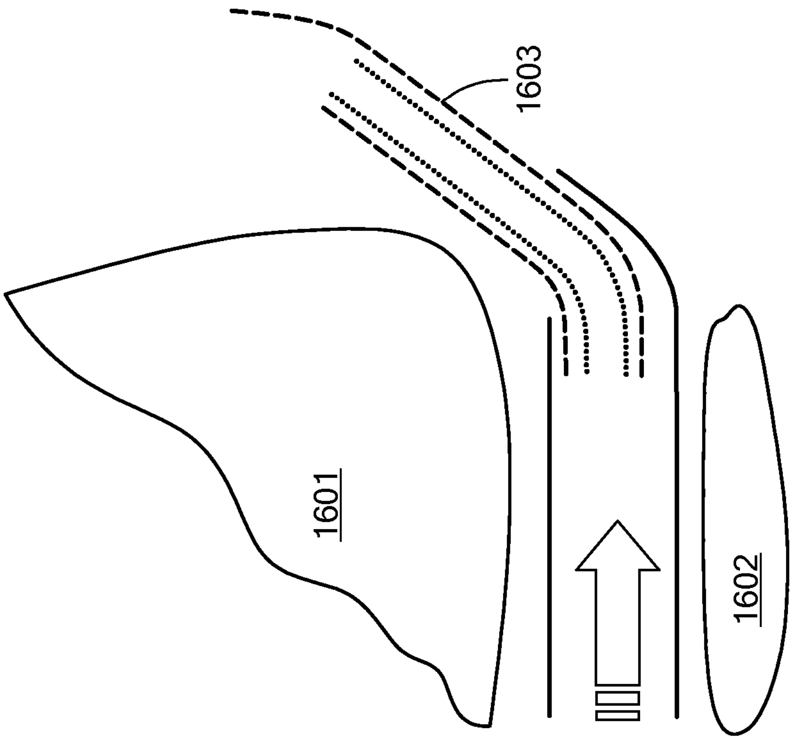
Figure 16D:
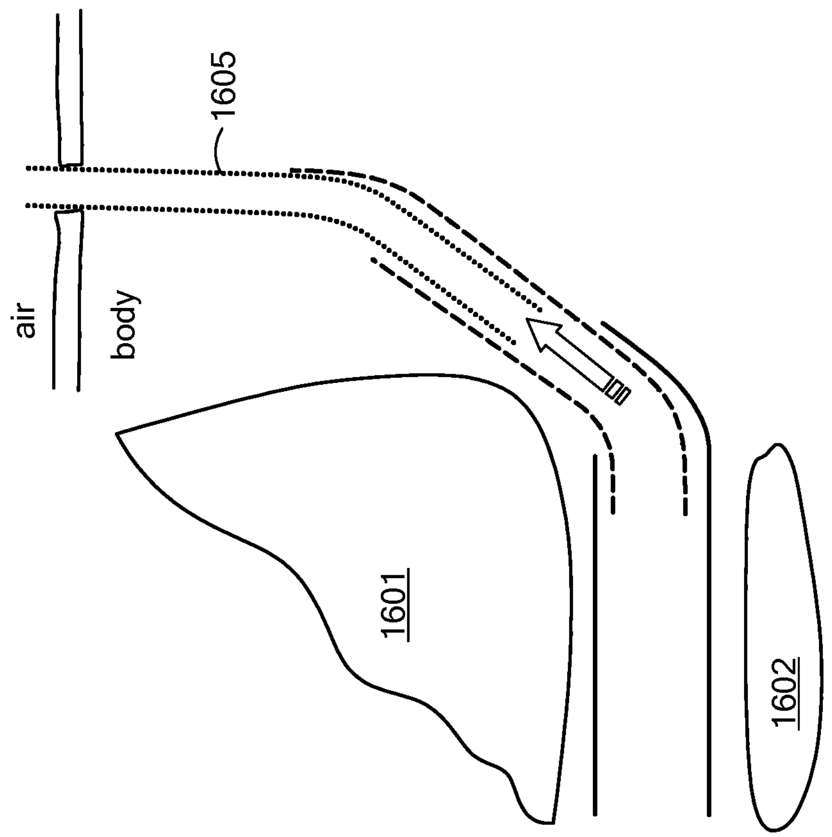
Figure 16F:
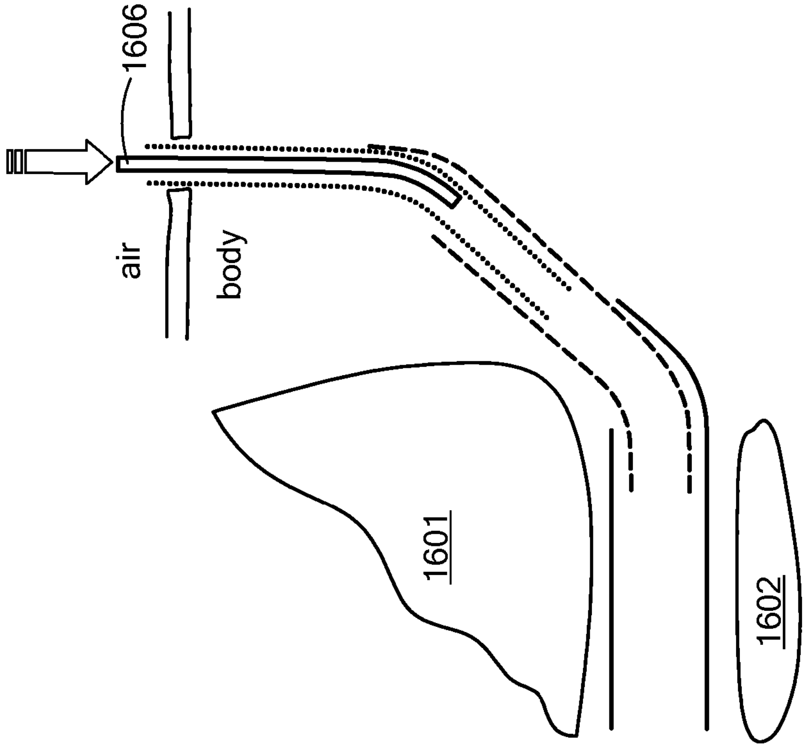
Figure 16E:
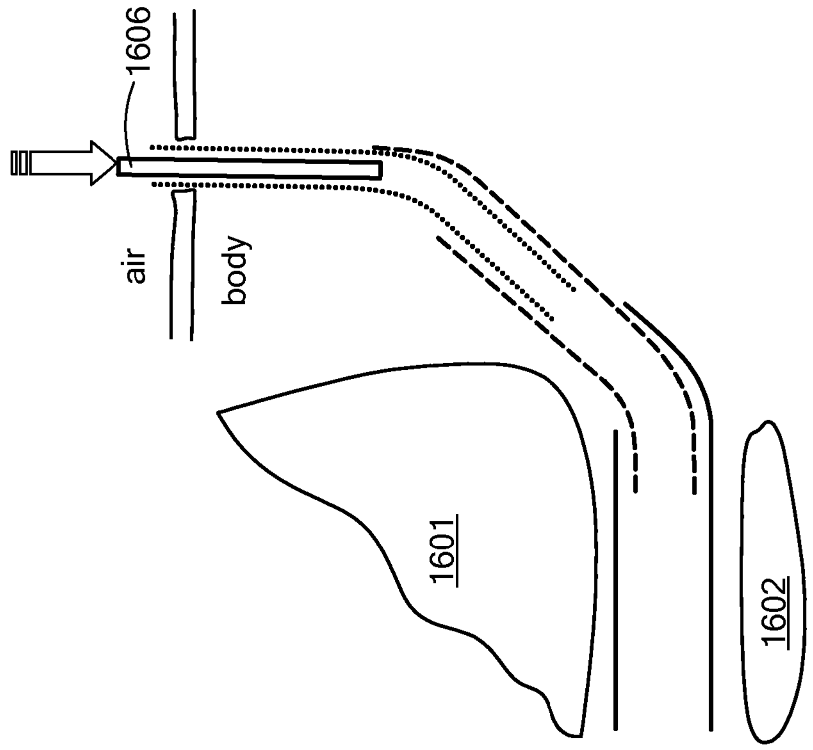
Figure 16H:
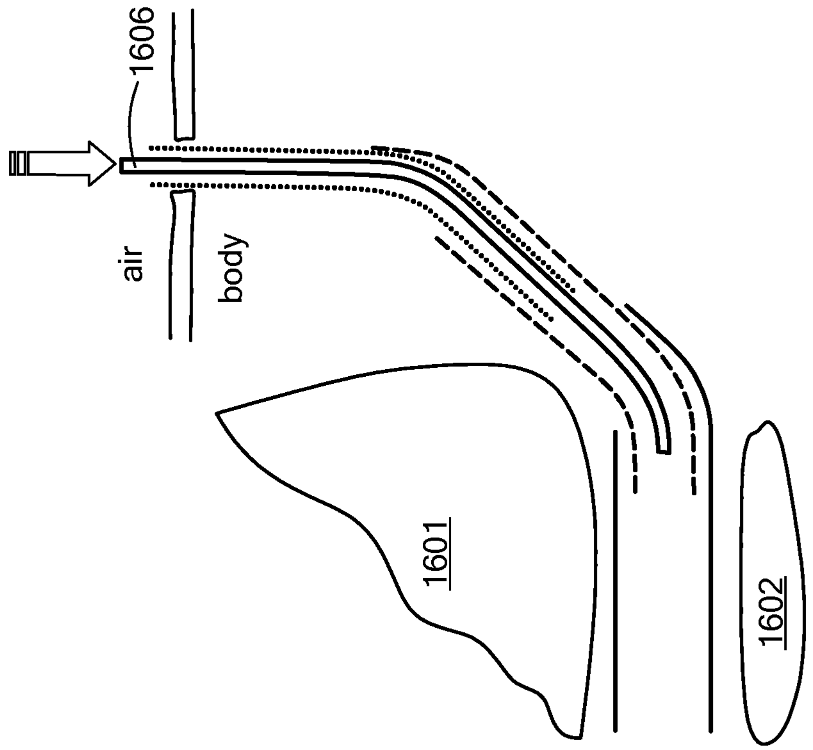
Figure 16G:
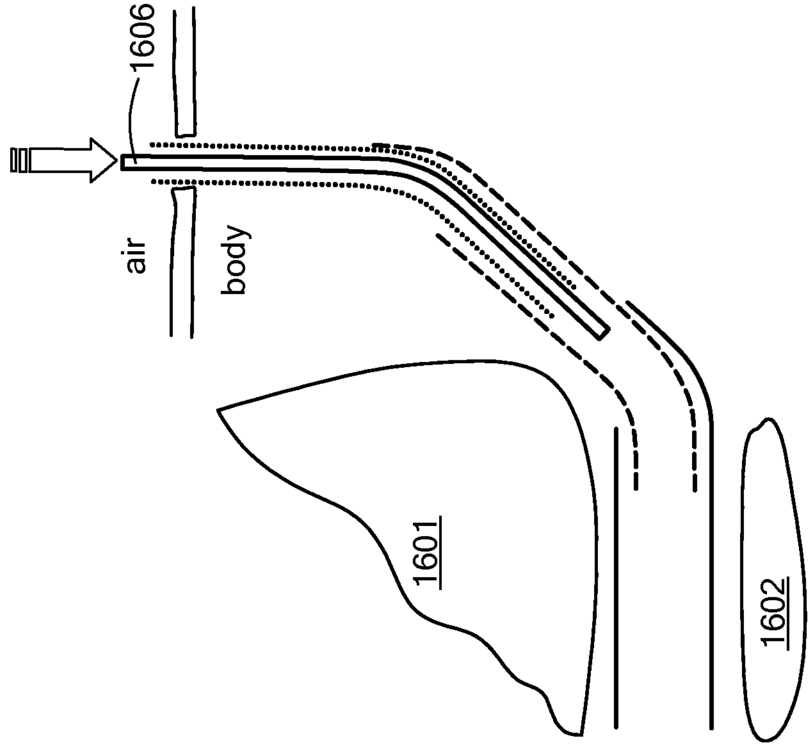
Figure 16J:
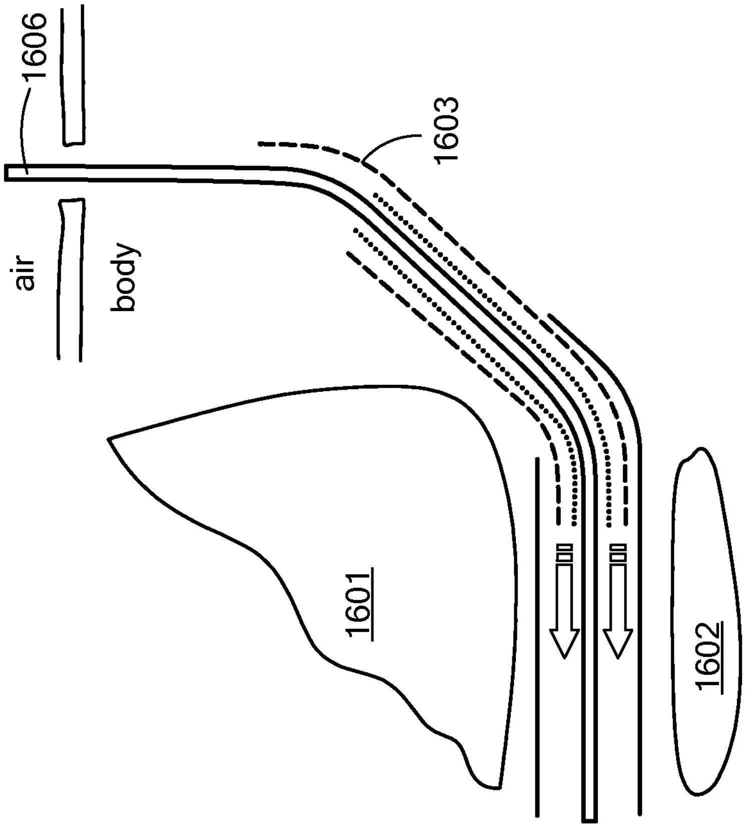
Figure 16I:
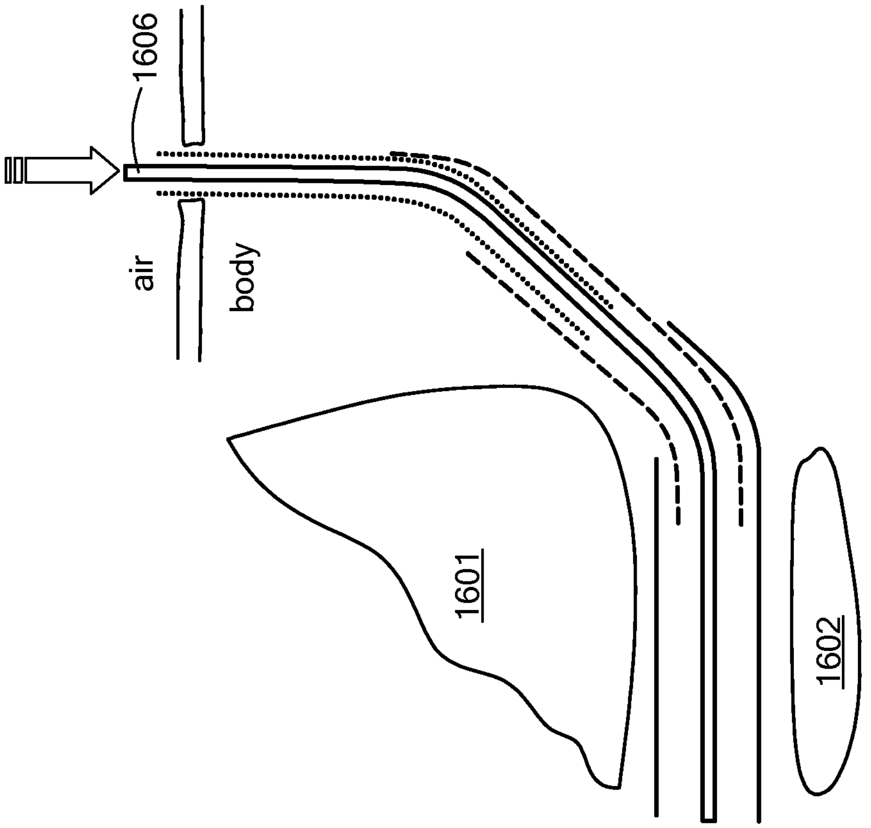
Figure 16L:
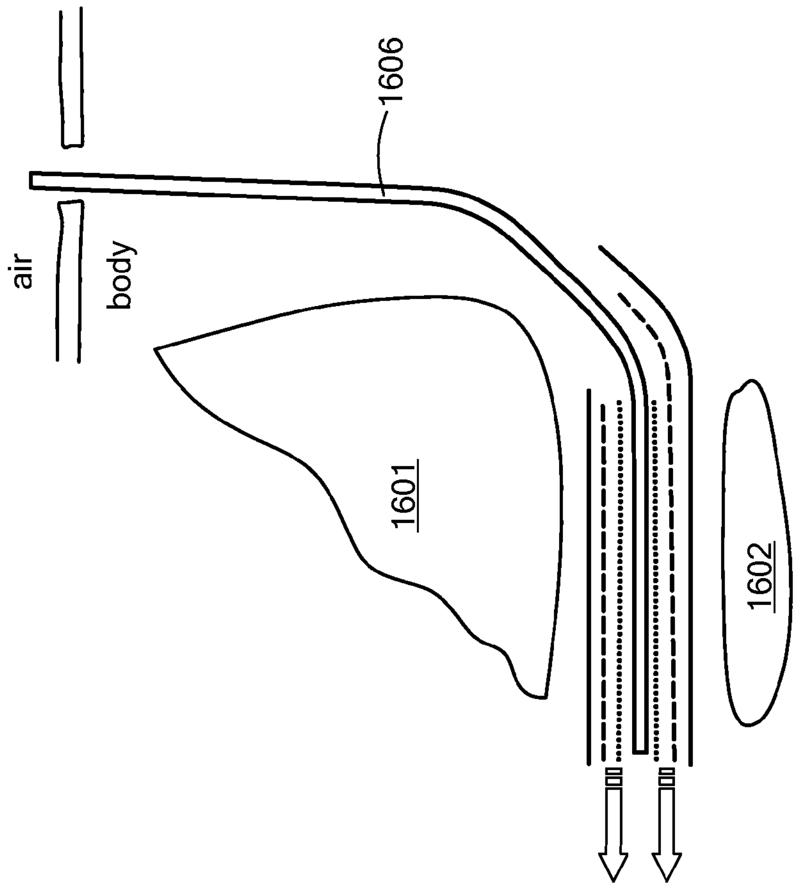
Figure 16K:
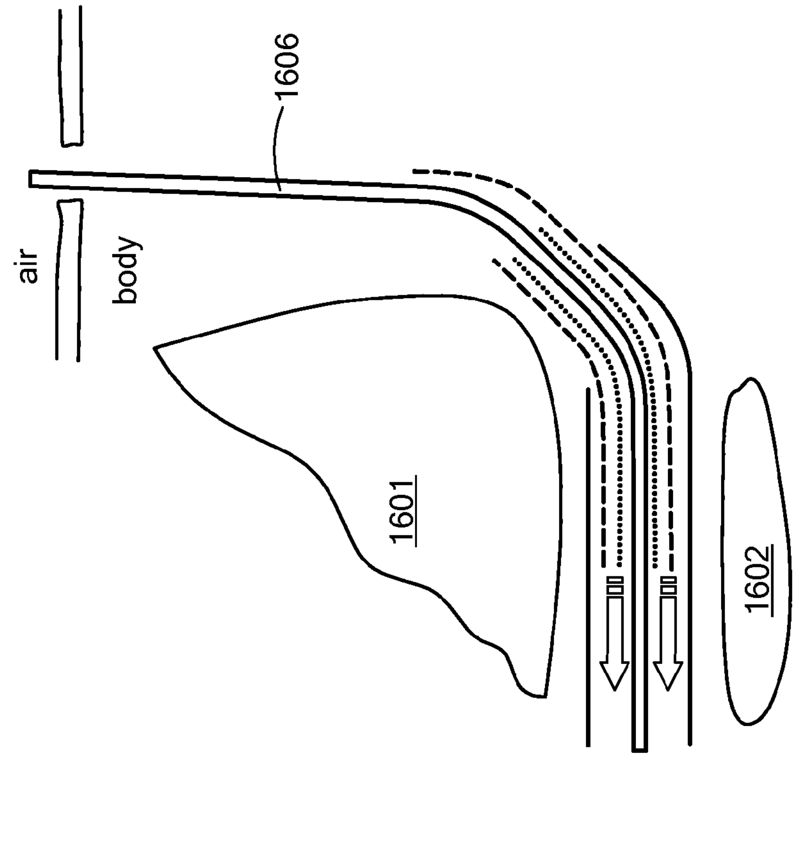
Figure 16M:
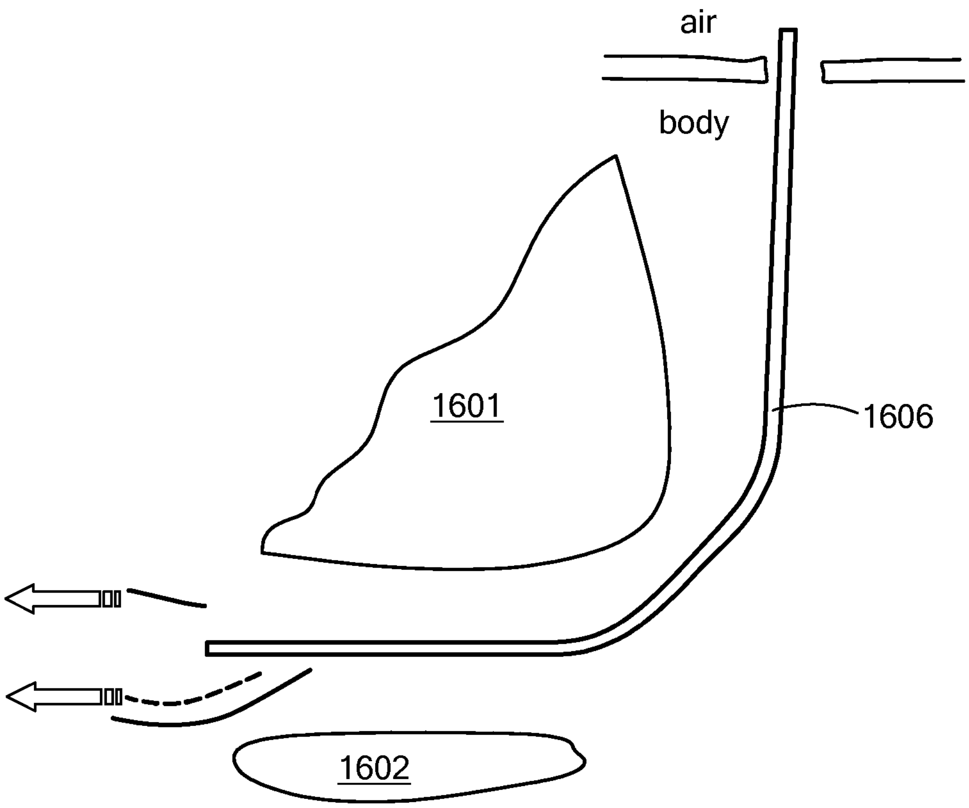
Figure 17A:
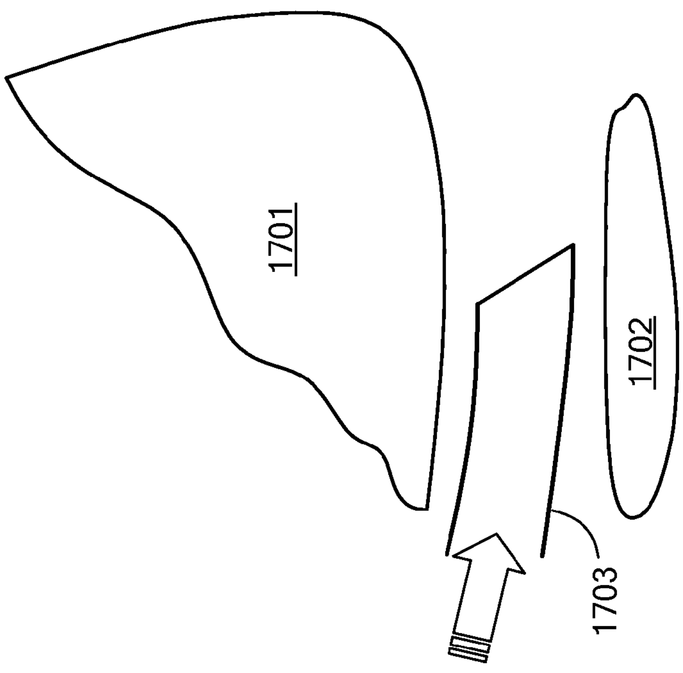
FIGS. 17A-H show a lateral view of the larynx and the insertion path of an interface element between muscle and cartilage according to illustrative embodiments of the present invention.
Figure 17B:
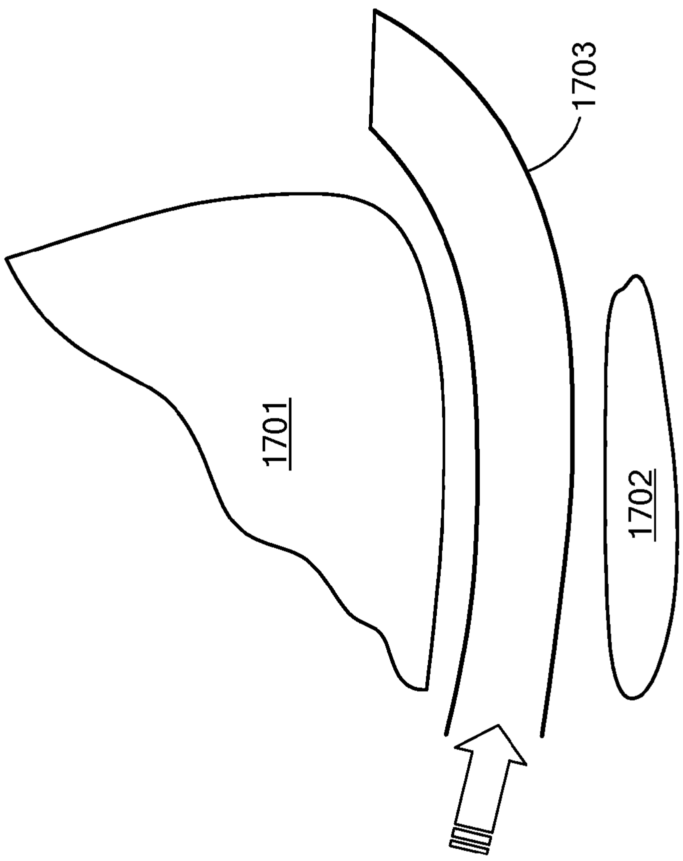
Figure 17C:
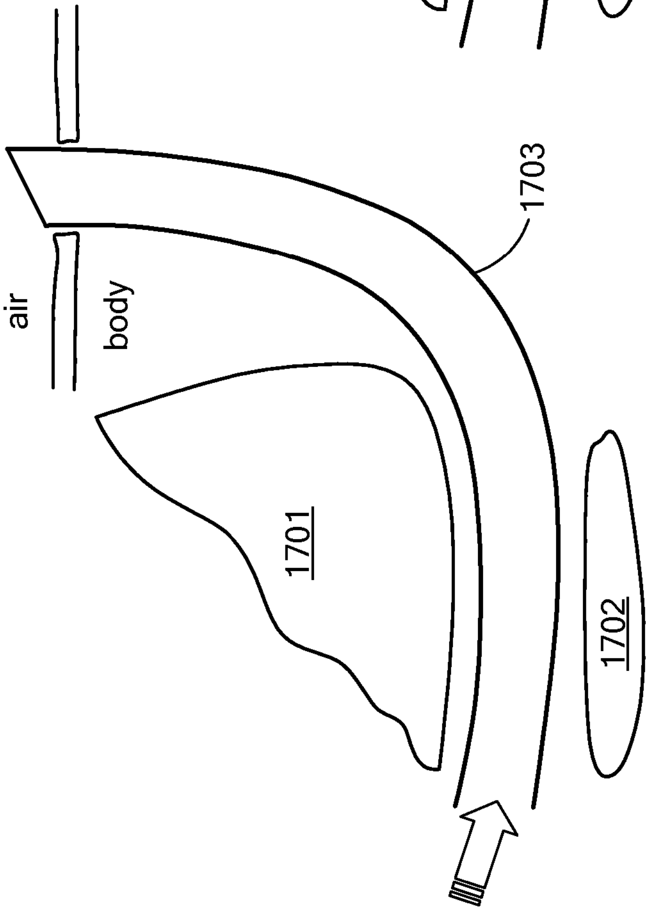
Figure 17D:
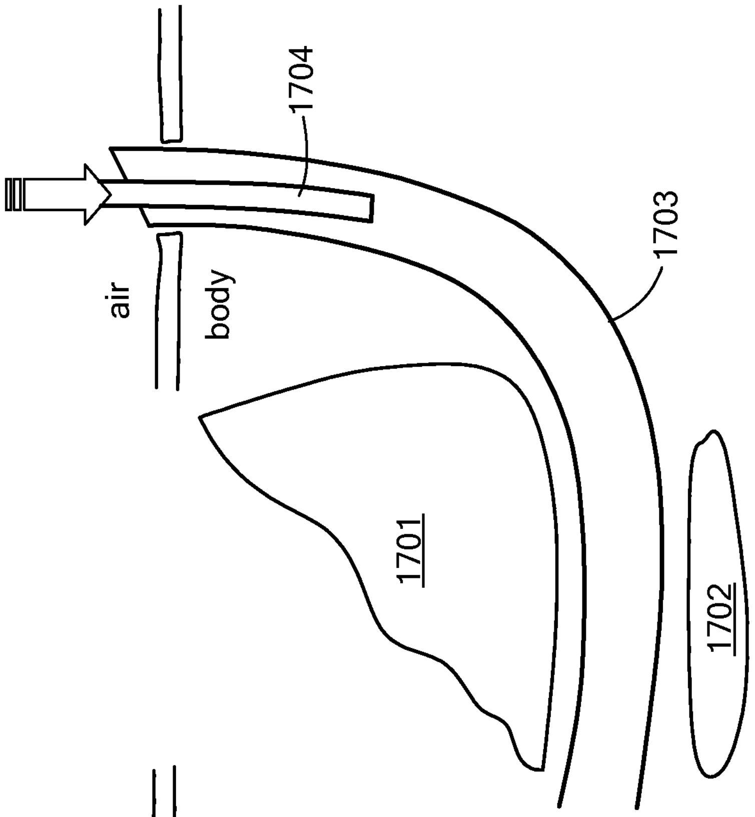
Figure 17F:
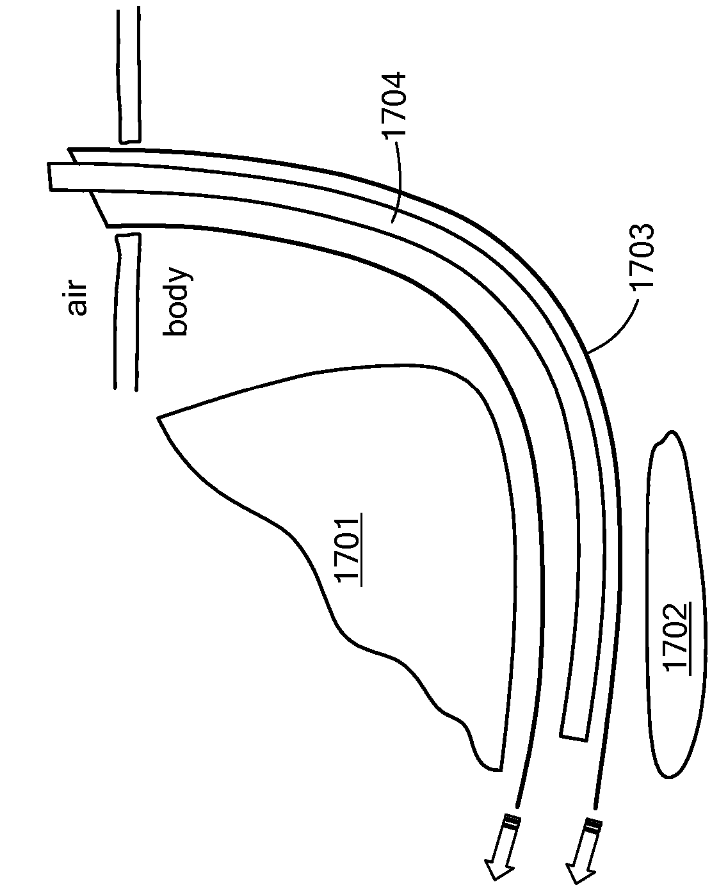
Figure 17E:
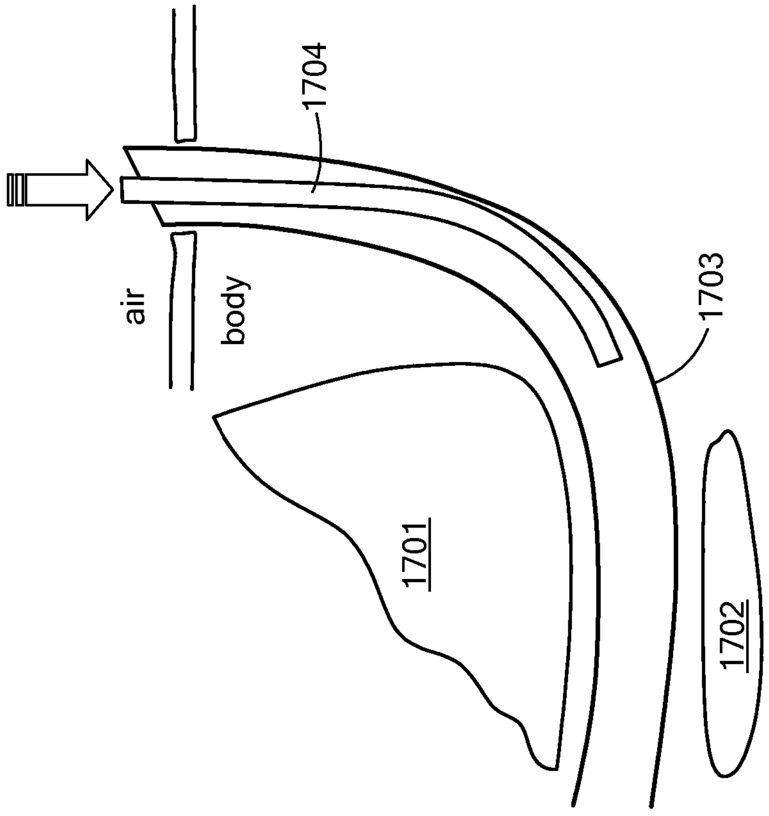
Figure 17H:
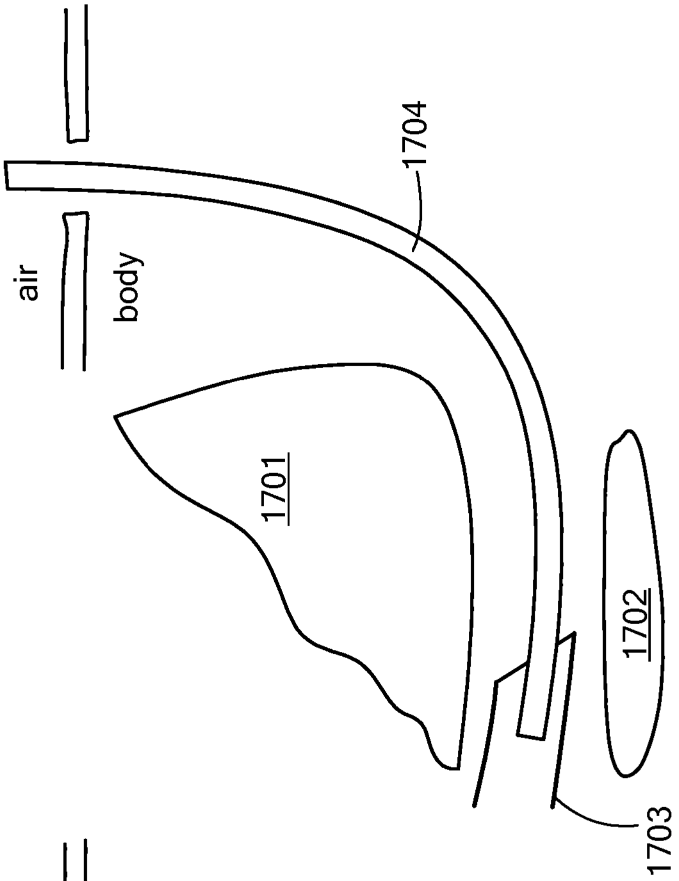
Figure 17G:
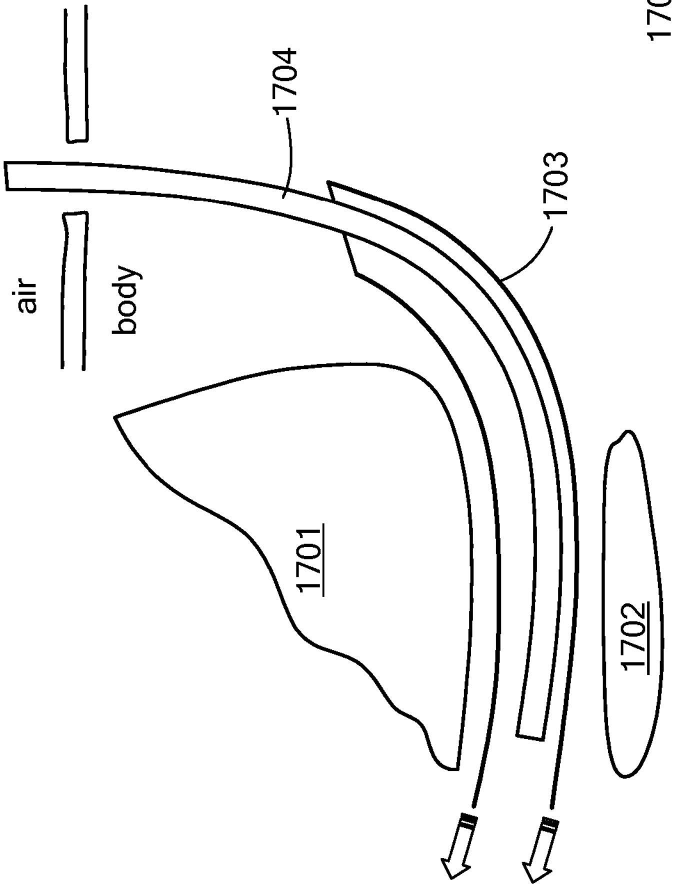

Embodiments of the present invention may also include an insertion system comprising a telescopic curved needle system for inserting an interface element in a subject. The telescopic curved needle system includes one or more inner hollow needles having successively smaller diameters than the outer portion of the telescopic curved needle system and located inside of the outer portion. FIGS. 16A-16M show the telescopic curved needle system at various stages during an insertion procedure. At the beginning of the procedure, the telescopic curved needle system may initially be relatively straight when in its unexpanded form as shown in FIG. 16A. The telescopic curved needle system may be inserted from outside of the body through a small incision in the skin or by starting from cavities inside the body like the pharynx, the stomach, the colon and the like. The relatively straight telescopic curved needle system may then be pushed forward in a pre-planed angle or under the control of a navigation tool (e.g., by palpation, x-ray, CT, MRI-navigation or the use of electrical test stimulators) with a certain force or speed until a certain length of the telescopic curved needle system is inserted, or a landmark, e.g., a bone, a cartilage and the like, is reached, or a target shown by the navigation tool is reached. For example, under direct or endoscopic laryngoscopic view, the relatively straight, unexpanded telescopic curved needle system may be inserted into the backside of the larynx so that it is pushed in-between the PCA muscle and the cricoid cartilage.

The first inner hollow needle 1603, which is totally hidden inside the outer portion of the telescopic curved needle system and has a smaller diameter than the outer portion, may then be pushed out of the tip of the outer hollow needle 1604, which may stay in place. The first inner hollow needle 1603 may be pushed with a certain force or speed until a certain length of the telescopic curved needle system is inserted, or a landmark, e.g., a bone, a cartilage and the like, is reached, or a target shown by the navigation tool is reached. For example, after inserting the relatively straight, unexpanded telescopic curved needle system deep enough to be outside the space in-between the muscle 1602 and the cartilage 1601 (on the other side of the muscle than the insertion point was) and to reach the lower posterior lateral edge of the cricoid cartilage near the crico-thyroid joint, the first inner hollow needle 1603 may be pushed out of the tip of the outer portion of the telescopic curved needle system with a certain force or speed until the first inner hollow needle 1603 reaches a desired position, e.g., leaves the body through the skin without hurting any important structure on its way through the tissue.

The telescopic curved needle system may not need to be further extended if a desired length or target is reached. However, if one extension or edge of the telescopic curved needle system is not enough to reach the target, then a second inner hollow needle 1605, which is inside the first inner hollow needle and has a smaller diameter than the first inner hollow needle, may be pushed out of the tip of the first inner hollow needle 1603, which may stay in place. The second inner hollow needle 1605 may be pushed with a certain force or speed until a certain length of the telescopic curved needle system is inserted, or a landmark, e.g., a bone, a cartilage and the like, is reached, or a target shown by the navigation tool is reached.

For example, if a second extension or edge is preferred after the edge near the cricoid joint then a second inner hollow needle 1605 may be used and pushed out of the tip of the first inner hollow needle 1603 with a certain force or speed until the second inner hollow needle 1605 reaches a desired position, e.g., leaves the body through the skin without hurting any important structure on its way through the tissue. The telescopic curved needle system may include additional inner needles if necessary.

After the inner hollow needle 1603 or 1605 leaves the body through the skin, an electrical stimulation electrode 1606, e.g., with contacts in a row along the tip of the electrode 1606, may be inserted inside the whole electrode insertion system of hollow needles. The electrode 1606 may be inserted until the electrode's tip is positioned in a desired location, e.g., in-between the PCA muscle 1602 and the cricoid cartilage 1601, or even further to the insertion point of the curved needle system (it may even look outside the skin in the larynx). The curved needle system may then be retracted back into the laryngeal side of original needle insertion while keeping the electrode 1606 in position, e.g., by fixing it at the insertion point of the electrode 1606, for example, manually. Alternatively, the curved needle system may be retracted while placing the electrode 1606 in a desired position. When the curved needle system is totally extracted and the electrode 1606 is in its desired positioned, e.g., on its way in-between the posterior cricoid muscle 1602 and the cricoid cartilage 1601, electrical energy may be transmitted through the electrode 1606. The electrical energy may be transmitted sequentially over one after the other electrical contact pads near the tip of the electrode 1606. The position of the electrode 1606 may then be corrected or optimized by visually controlling the movement of the vocal cord in response to electrical stimulation and retracting the electrode 1606, if necessary. Alternatively, electrical energy may be transmitted through the electrode 1606 before the curved needle system is totally extracted, thus allowing optimization of the electrode 1606 position both by retracting and/or inserting the electrode 1606.

A stimulation device 1806, such as a pacemaker (see FIG. 18) may then be implanted via a small subcutaneous tunnel into a subcutaneous pocket. The insertion system including a telescopic curved needle system may be used in a variety of ways and applications, e.g., inserting an interface element as shown in FIGS. 1-8.

Embodiments of the present invention may include an insertion system comprising a straight needle system or a curved needle system for inserting an interface element in a subject. FIGS. 17A-H show a curved needle system at various stages during an insertion procedure. As shown, the procedure begins by inserting the curved needle system 1703 from outside of the body through a small incision in the skin or by starting from cavities inside the body like the pharynx, the stomach, the colon and the like. The curved needle system 1703 may then be pushed forward in a pre-planned angle or under the control of a navigation tool or via the help of landmarks (e.g., a bone, a cartilage and the like) with a certain force or speed until a certain length of the curved needle system is inserted, the landmark is reached, or a target shown by the navigation tool is reached. The navigation tool may include palpation, x-ray, CT or MRI navigation or the use of electrical test stimulators connected to the interface element 1704. For example, the stimulator may emit electrical energy via one or more contacts positioned at the tip of the interface element 1704, at selected areas along the interface element 1704 (e.g., at non-insulated areas when the element includes insulated and non-insulated areas) or along the whole interface element 1704 (e.g., when the element is not insulated).

Under direct or endoscopic laryngoscopic view, the curved needle system may be inserted into the backside of the larynx so that it is pushed in-between the PCA muscle 1702 and the cricoid cartilage 1701. After inserting the curved needle system 1703 deep enough to be outside the space in-between the muscle 1702 and the cartilage 1701 (on the other side of the muscle than the insertion point was) and to reach the lower posterior lateral edge of the cricoid cartilage near the crico-thyroid joint, the curved needle system 1703 may turn around this edge of the cartilage 1701 because of its pre-curved shape. The curved needle system 1703 may be pushed further until it reaches a desired position, e.g., leaves the body through the skin without hurting any important structure on its way through the tissue.

After the curved needle system 1703 leaves the body through the skin, an interface element 1704 such as an electrical stimulation electrode (e.g., with contacts in a row along the tip of the electrode) or a catheter, may be inserted inside the curved needle system. In another embodiment, an interface element 1704 is fixed to the tip of the curved needle system 1703 by a thread and the interface element 1704 is inserted from the outside by pulling the curved needle system 1703 back and thereby pulling the interface element 1704 back through the tissue via the connected thread. The interface element 1704 may be inserted until the element's tip is positioned in a desired location, e.g., in-between the PCA muscle 1702 and the cricoid cartilage 1701, or even further to the insertion point of the curved needle system 1703 (it may even look outside the skin in the larynx). The curved needle system 1703 may then be retracted back into the laryngeal side of original needle insertion while keeping the interface element 1704 in position, e.g., by fixing it at the insertion point of the interface element 1704, for example, manually. Alternatively, the curved needle system 1703 may be retracted while placing the interface element 1704 in a desired position. When the curved needle system 1703 is totally extracted and the interface element 1704 is in its desired positioned, e.g., on its way in-between the PCA muscle 1702 and the cricoid cartilage 1701, an item may be transmitted through the interface element 1704, such as electrical energy through an electrode or a drug through a catheter. Electrical energy may be transmitted sequentially over one after the other electrical contact pads near the tip of the electrode. The position of the interface element 1704 may then be corrected or optimized by visually controlling the movement of the vocal cord in response to the transmitted item (e.g., electrical stimulation) interacting with the vocal cord, and retracting the interface element 1704, if necessary. Alternatively, the item may be transmitted through the interface element 1704 before the curved needle system 1703 is completely extracted, thus allowing optimization of the interface element 1704 position both by retracting and/or inserting the interface element 1704, if necessary.

The pacer 1806 may then be implanted via a small subcutaneous tunnel into a subcutaneous pocket. Embodiments of the present invention also permit a minimally invasive, two stage implantation procedure to be possible. First, an interface element 1704, e.g., an electrode, may be inserted as disclosed above, but the stimulator itself is not implanted during the same surgery but left outside the body. A test stimulation session may then be performed over time, e.g., several days or even weeks. If this test stimulation period shows efficiency, the pacer may be sterilized, the electrodes may be connected to the pacer 1806 via a small subcutaneous tunnel, and the pacer may then be implanted into the subcutaneous pocket. If the test stimulation period shows not enough efficiency, then the electrode may be retracted out of the body without a complicated surgery by simply pulling the electrode back till its tip leaves the skin. The insertion system including a curved needle system 1703 may be used in a variety of ways, e.g., inserting an interface element 1704 as shown in FIGS. 1-8 and FIG. 18.

Although various exemplary embodiments of the invention have been disclosed, it should be apparent to those skilled in the art that various changes and modifications may be made which will achieve some of the advantages of the invention without departing from the true scope of the invention.

What is claimed is:

1. A method of positioning a laryngeal interface element for interfacing with a laryngeal structure of a subject, the method comprising:

forming a tunnel through thyroid cartilage and forming a subperichondral tunnel on an inside of the thyroid cartilage toward a cricothyroid joint of the subject to generate an interface insertion path with respect to vocal cord cartilage of the subject; and positioning the interface element relative to the laryngeal structure of the subject based on the insertion path.

2. A method according to claim 1, further comprising:

interfacing the interface element with the laryngeal structure.

3. A method according to claim 2, wherein interfacing the interface element includes delivering a drug to the laryngeal structure via the interface element.

4. A method according to claim 2, further comprising:

routing a portion of the interface element percutaneously through the skin of the subject to the outside of the subject, and connecting the interface element to an external verification device to verify efficacy of the interfacing with laryngeal structures.

5. A method according to claim 1, further comprising:

coupling the interface element to an implantable interface controller in communication with the interface element.

6. A method according to claim 1, wherein the insertion path ends between cricoid cartilage and posterior cricoarytenoid muscle.

7. A method according to claim 1, wherein the laryngeal structure includes a vocal cord, both vocal cords, an epiglottis, a pharyngeal constrictor, a supraglottic sphincter, or a combination thereof.

8. A method according to claim 1, wherein the laryngeal structure includes a muscle, a nerve, or both.

9. A method according to claim 1, wherein the interface element includes an electrode, a sensor, a catheter, or a combination thereof.

* * * * *